United States Patent
Commerçon et al.

(10) Patent No.: US 8,314,142 B2
(45) Date of Patent: Nov. 20, 2012

(54) DIMERS OF ARTEMISININ DERIVATIVES, PREPARATION THEREOF AND THERAPEUTIC USE THEREOF

(75) Inventors: Alain Commerçon, Vitry-sur-Seine (FR); Jidong Zhang, Paris (FR); Augustin Hittinger, Igny (FR)

(73) Assignee: Sanofi, Paris (FR)

( * ) Notice: Subject to any disclaimer, the term of this patent is extended or adjusted under 35 U.S.C. 154(b) by 948 days.

(21) Appl. No.: 12/244,225

(22) Filed: Oct. 2, 2008

(65) Prior Publication Data

US 2009/0082426 A1 Mar. 26, 2009

Related U.S. Application Data

(63) Continuation of application No. PCT/FR2007/000585, filed on Apr. 6, 2007.

(30) Foreign Application Priority Data

Apr. 11, 2006 (FR) ...................... 06 03209

(51) Int. Cl.
*C07D 309/00* (2006.01)
*A61K 31/335* (2006.01)
(52) U.S. Cl. ...................... 514/450; 549/358
(58) Field of Classification Search .............. 549/348; 514/450

See application file for complete search history.

(56) References Cited

U.S. PATENT DOCUMENTS

| 6,307,068 B1 | 10/2001 | Li et al. |
| 6,790,863 B2 | 9/2004 | ElSohly et al. |
| 7,842,720 B2 * | 11/2010 | Elsohly et al. ................. 514/450 |
| 2005/0038024 A1 | 2/2005 | Begue et al. |

FOREIGN PATENT DOCUMENTS

| CN | 1239097 A | 12/1999 |
| CN | 101125142 A | 2/2008 |
| WO | WO 99/65914 | 12/1999 |

OTHER PUBLICATIONS

Jung et al, Antitumor Activity of Novel Deoxoartemisinin Monomers, Dimers, and Trimer, J. Med. Chem., 2003, 46, pp. 987-994.
Posner et al, Trioxane Dimers Have Potent Antimalarial, Antiproliferative and Antitumor Activities In Vitro, Bioorganic & Medicinal Chemistry, vol. 5, No. 7, pp. 1257-1265, 1997.
International Search Report for WO2007/116135 dated Oct. 18, 2007.
The Role of Artemisinin and its Derivatives in the Current Treatment of Malaria (1994-1995), World Health Organization (WHO), Geneva. Sep. 27-29, 1993, pp. 1-52.
La Artemisina Y Sus Derivados En El Tratamiento De La Malaria (1994-1995), WHO, World Health Organization, Geneva, Sep. 27-29, 1993, pp. 1-59.

* cited by examiner

*Primary Examiner* — Andrew D Kosar
*Assistant Examiner* — Raymond Covington

(57) ABSTRACT

The present invention relates to dimers of artemisinin derivatives, to processes for the preparation of such dimers, to methods of treatment comprising administration of such dimers, and to intermediates to such dimers.

13 Claims, No Drawings

DIMERS OF ARTEMISININ DERIVATIVES, PREPARATION THEREOF AND THERAPEUTIC USE THEREOF

The present invention relates to dimers of artemisinin derivatives, their preparation and their therapeutic application.

More particularly, the invention relates to dimers of artemisinin derivatives having an anticancer activity, and in particular a cell proliferation inhibiting activity.

Currently, most commercial compounds used in chemotherapy have major problems of side effects, of tolerance by patients or of resistance. Thus, there is a great need for novel classes of compounds capable of acting as anticancer agents.

Among natural products, artemisinin is a sesquiterpene endoperoxide which was isolated in 1971 from the plant *Artemisia annua* and has antimalarial properties. Some simple derivatives, such as dihydroartemisinin or artemether, have been prepared and also have antimalarial properties. In addition to this activity, it has been shown that some artemisin derivatives and dimers have anticancer properties (J. Med. Chem. 2003, 46, 987-994; U.S. Pat. No. 6,790,863).

The problem which the present invention proposes to solve is to obtain novel products in the form of artemisinin dimers having an anticancer activity.

The subject of the present invention is products corresponding to the general formula (I)

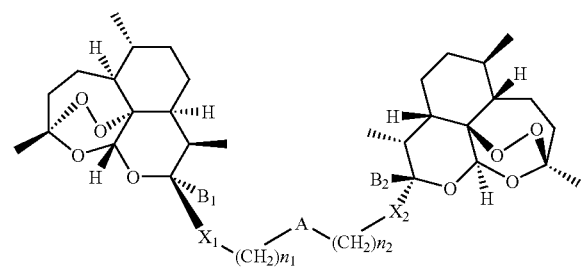

(I)

in which:
  a) A is a divalent group chosen from —S—, —SO—, —SO$_2$—, —NR$_a$—, —N$^+$(O$^-$)R$_a$—, —CONR$_a$—, —NR$_a$SO$_2$—, —CO—, —COO—, —NR$_a$CONR$_b$—, —NR$_a$SO$_2$NR$_b$—, —OP(O)(OR$_a$)O—, —OCONR$_a$—, —OCOO—, —O—, —C(=N—OR$_a$)—, or an epoxide, (C$_1$-C$_6$)alkylene, (C$_1$-C$_6$)alkenylene, (C$_1$-C$_6$)alkynylene, (C$_3$-C$_8$)cycloalkylene, (C$_4$-C$_8$)cycloalkenylene, arylene, heteroarylene or heterocyclyl group, it being possible for these last nine groups to be optionally substituted with one or more substituents R$_a$ or R$_b$;
  b) X$_1$ and X$_2$ are identical or different, and are chosen from N, O, S;
  c) B$_1$ and B$_2$ are identical or different and represent a —(CF$_2$)$_p$—R$_c$ in which R$_c$ is independently F, (C$_1$-C$_6$) alkyl, (C$_1$-C$_6$)alkenyl, (C$_1$-C$_6$)alkynyl, (C$_3$-C$_8$)cycloalkyl, (C$_4$-C$_8$)cycloalkenyl, aryl, heteroaryl, heterocyclyl, —COR$_1$, —COOR$_1$, —CONR$_1$R$_2$, —OR$_1$ or —SR$_1$, it being possible for these groups to be optionally substituted with one or more substituents R$_a$ or R$_b$, which are identical or different, and p has the value 1, 2 or 3;
  d) n$_1$ and n$_2$ are identical or different and have the value 0, 1, 2, 3 or 4;
  e) R$_a$ and R$_b$ are identical or different and are independently chosen from: H, halogen, —(C$_1$-C$_6$)alkyl, —(C$_1$-C$_6$)alkyl-COO—R$_1$, —(C$_1$-C$_6$)alkyl-NR$_1$R$_2$, —(C$_1$-C$_6$)alkylaryl, —(C$_1$-C$_6$)alkenyl, —(C$_1$-C$_6$)alkynyl, aryl, heteroaryl, (C$_3$-C$_8$)cycloalkyl, (C$_4$-C$_8$)cycloalkenyl, heterocyclyl, —OR$_1$, —OCOR$_1$, —COR$_1$, —COOR$_1$, —CONR$_1$R$_2$, —NR$_1$R$_2$, —NR$_1$COR$_2$, —SR$_1$, —SO$_2$R$_1$, —CN;
  f) R$_1$ and R$_2$ are identical or different and are independently chosen from H, (C$_1$-C$_6$)alkyl, (C$_1$-C$_6$)alkenyl, (C$_1$-C$_6$) alkynyl, (C$_3$-C$_8$)cycloalkyl, (C$_4$-C$_8$)cycloalkenyl, aryl, heteroaryl, heterocyclyl;

in the form of a base or of an addition salt with an acid, and in the form of a hydrate or a solvate.

None of these dimers of the prior art (J. Med. Chem. 2003, 46, 987-994; U.S. Pat. No. 6,790,863) is substituted with a B$_1$ or B$_2$ group as described above according to the present invention.

Among the products of general formula (I) which are the subject of the invention, there may be mentioned in particular the products for which B$_1$ and B$_2$ are identical and are CF$_3$.

Among the products of general formula (I) which are the subject of the invention, there may also be mentioned the products of general formula (I) for which X$_1$ and X$_2$ are identical and are O.

Among these products, preferred products are those for which A is —S—, —SO— or —SO$_2$—.

Other products of general formula (I) are those for which A is —N(CH$_3$)—.

According to the present invention, n$_1$ and n$_2$ are preferably identical and have the value 2, 3 or 4.

Other products of general formula (I) are those for which A is chosen from —NH—, —N(CH$_2$—C(O)O—CH$_2$—CH$_3$)— or —N(CH$_2$—COOH)—, and optionally characterized in that n$_1$ and n$_2$ are identical and have the value 2.

Other products of general formula (I) are those for which A is chosen from (C$_1$-C$_6$)alkenylene or epoxide, and optionally characterized in that n$_1$ and n$_2$ are identical and have the value 1.

Other products of general formula (I) are those for which A is chosen from —NHCO— or -1,2,3-triazole, and optionally characterized in that n$_1$ and n$_2$ are different and independently have the value 1 or 2.

The products of formula (I) may contain one or more asymmetric carbon atoms. They can therefore exist in the form of enantiomers or diastereoisomers. These enantiomers, diastereoisomers and mixtures thereof, including the racemic mixtures, form part of the invention.

The products of formula (I) can exist in the form of bases or of addition salts with acids. Such addition salts form part of the invention.

These salts may be prepared with pharmaceutically acceptable acids, but the salts of other useful acids, for example, for the purification or isolation of the products of formula (I) also form part of the invention.

The products of formula (I) can also exist in the form of hydrates or solvates, namely in the form of associations or combinations with one or more molecules of water or with a solvent. Such hydrates and solvates also form part of the invention.

In the context of the present invention:
- a halogen atom is understood to mean: a fluorine, a chlorine, a bromine or an iodine;
- an alkyl group is understood to mean a saturated linear or branched aliphatic group. By way of examples, there may be mentioned the methyl, ethyl, propyl, isopropyl, butyl, isobutyl, tert-butyl and pentyl groups, and the like;
- a cycloalkyl group is understood to mean: a cyclic alkyl group. By way of examples, there may be mentioned the cyclopropyl, methylcyclopropyl, cyclobutyl, cyclopentyl and cyclohexyl groups, and the like;
- a fluoroalkyl group is understood to mean: an alkyl group in which one or more hydrogen atoms have been substituted with a fluorine atom;
- an alkenyl group is understood to mean: a mono- or polyunsaturated, linear or branched, aliphatic group comprising, for example, one or two ethylenic unsaturations;
- an alkynyl group is understood to mean: a mono- or polyunsaturated, linear or branched, aliphatic group comprising, for example, one or two acetylenic unsaturations;
- an alkoxy group is understood to mean: an —O-alkyl radical where the alkyl group is as defined above;
- an aryl group is understood to mean: a cyclic aromatic group comprising from 5 to 14 carbon atoms. The phenyl, naphth-1-yl; naphth-2-yl, anthracen-9-yl, 1,2,3,4-tetrahydronaphth-5-yl and 1,2,3,4-tetrahydronaphth-6-yl substituents are examples of aryl substituents;
- a heteroaryl group is understood to mean: a cyclic aromatic group comprising from 1 to 13 carbon atoms and from 1 to 4 heteroatoms. The pyrrol-1-yl, pyrrol-2-yl, pyrrol-3-yl, furyl, thienyl, imidazolyl, oxazolyl, thiazolyl, isoxazolyl, isothiazolyl, 1,2,4-triazolyl, oxadiazolyl, thiadiazolyl, tetrazolyl, pyridyl, pyrimidyl, pyrazinyl, 1,3,5-triazinyl, indolyl, benzo[b]furyl, benzo[b]thienyl, indazolyl, benzimidazolyl, azaindolyl, quinolyl, isoquinolyl, carbazolyl and acridyl substituents are examples of heteroaryl substituent. The term "heteroatom" refers here to an at least divalent atom different from carbon. N, O, S and Se are examples of heteroatom.
- a cycloalkyl group is understood to mean: a saturated or partially unsaturated cyclic hydrocarbon substituent having from 3 to 12 carbon atoms. The cyclopropyl, cyclobutyl, cyclopentyl, cyclopentenyl, cyclopentadienyl, cyclohexyl, cyclohexenyl, cycloheptyl, bicyclo[2.2.1]heptyl, cyclooctyl, bicyclo[2.2.2]octyl, adamantyl and perhydronaphthyl substituents are examples of cycloalkyl substituent.
- a heterocyclyl group is understood to mean: a saturated or partially unsaturated cyclic hydrocarbon substituent having from 1 to 13 carbon atoms and from 1 to 4 heteroatoms. Preferably, the saturated or partially unsaturated cyclic hydrocarbon substituent will be monocyclic and will contain 4 or 5 carbon atoms and 1 to 3 heteroatoms.

It is understood that the divalent group A is capable of being bonded in the two possible directions. For example, when the divalent group A is —NHSO$_2$—, the product of general formula (I) may be:

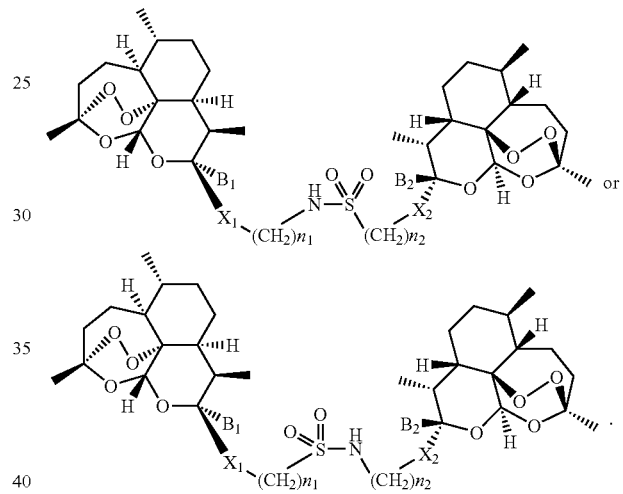

In accordance with the present invention, the products of general formula (I) may be prepared according to conventional methods of organic chemistry. Examples of synthesis are illustrated in schemes 1 to 4 below, in which the starting materials and reagents, when their mode of preparation is not described, are commercially available or are described in the literature or may be prepared according to methods which are described therein or which are known to persons skilled in the art.

Scheme 1

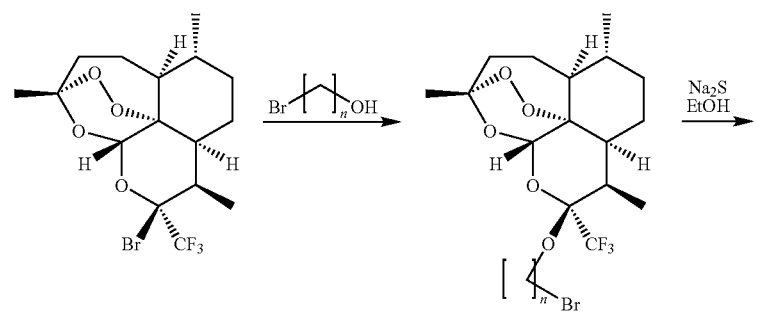

5 6
-continued
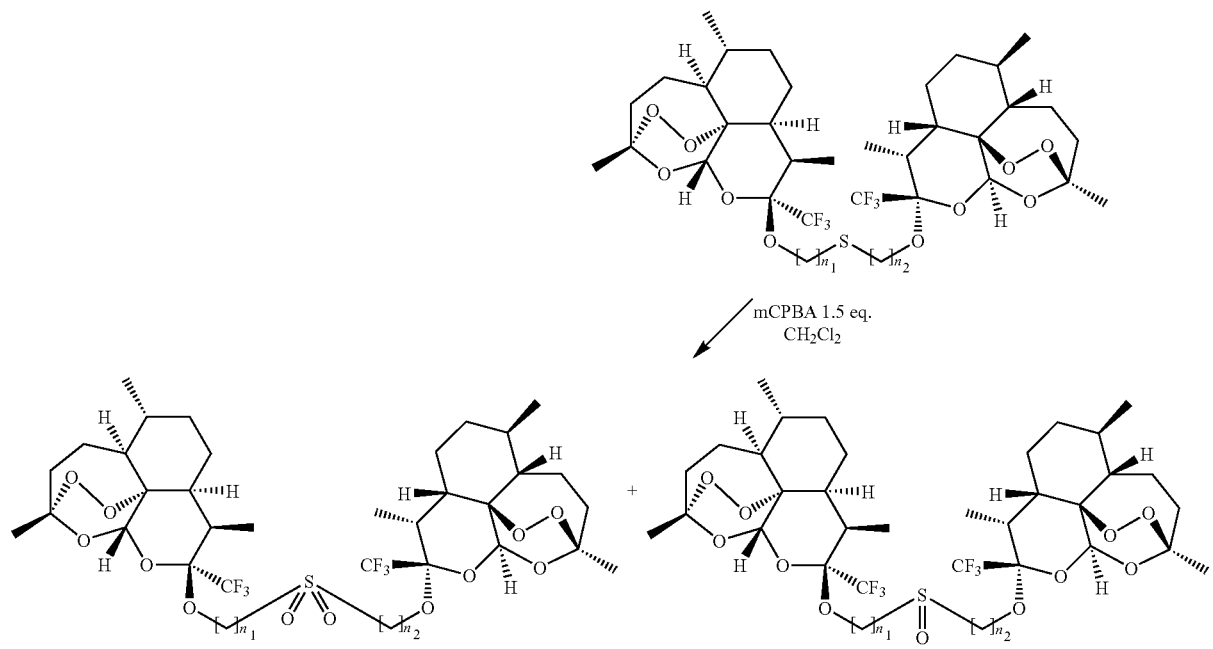
mCPBA 1.5 eq.
CH₂Cl₂
Scheme 2
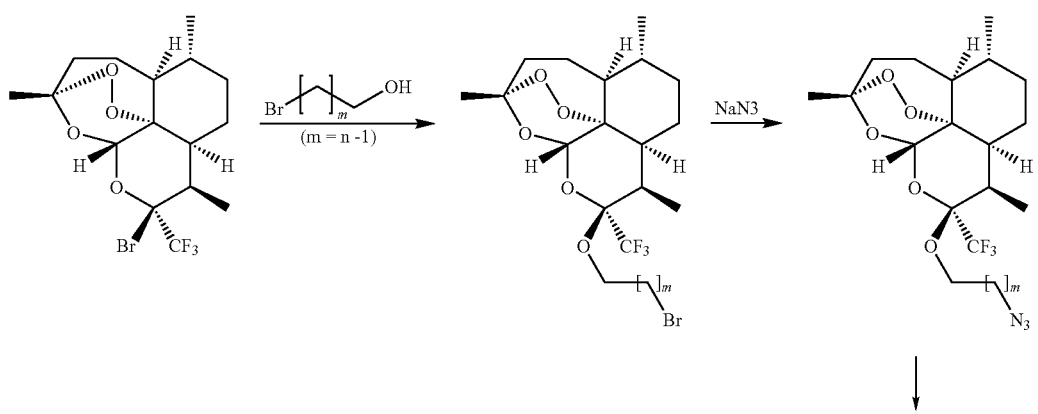
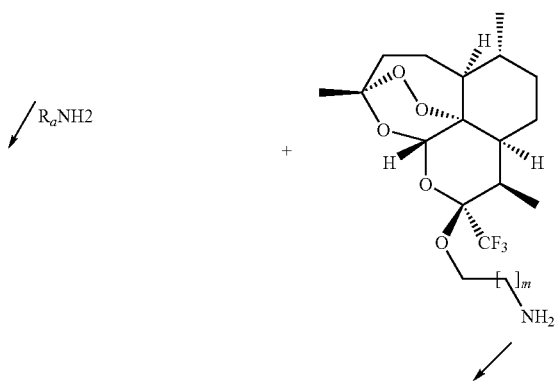

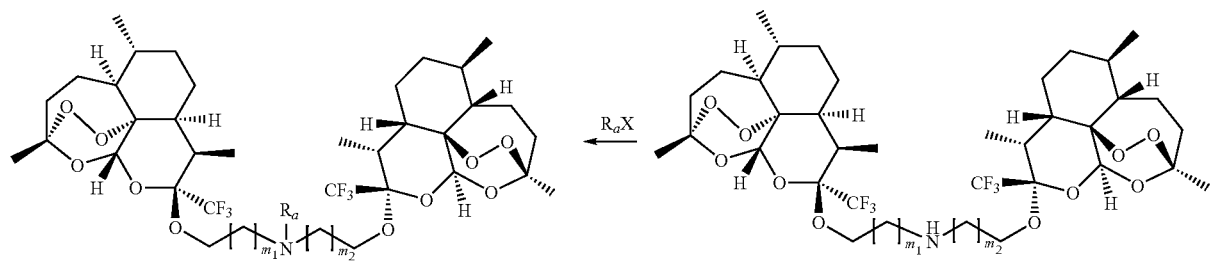
Scheme 3
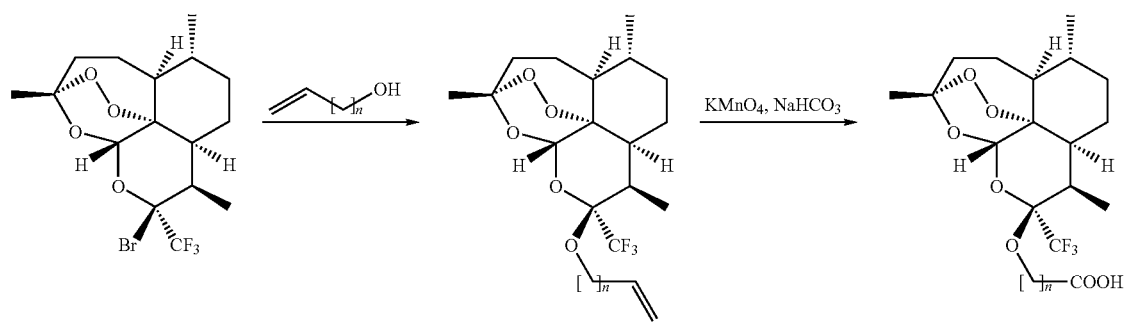
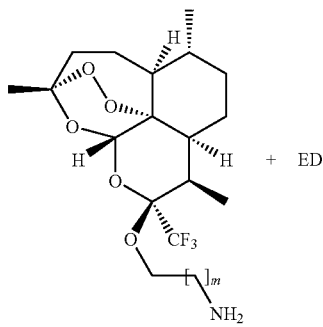
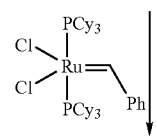
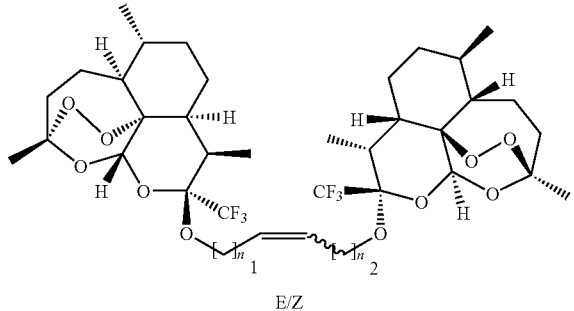
E/Z
↙ m-CPBA
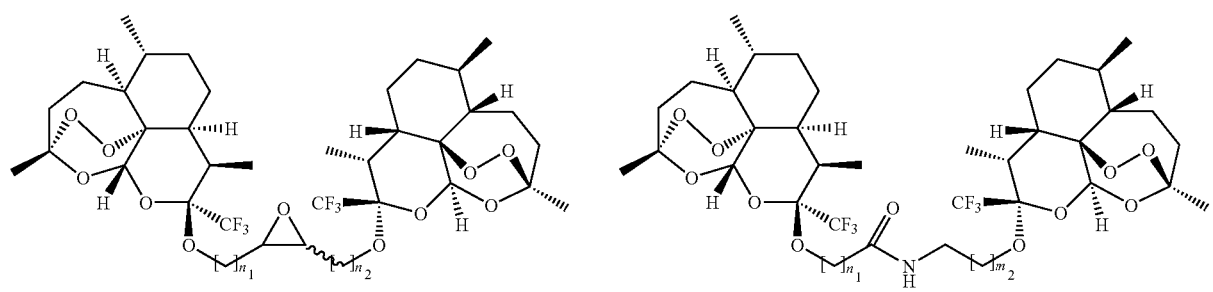

Scheme 4

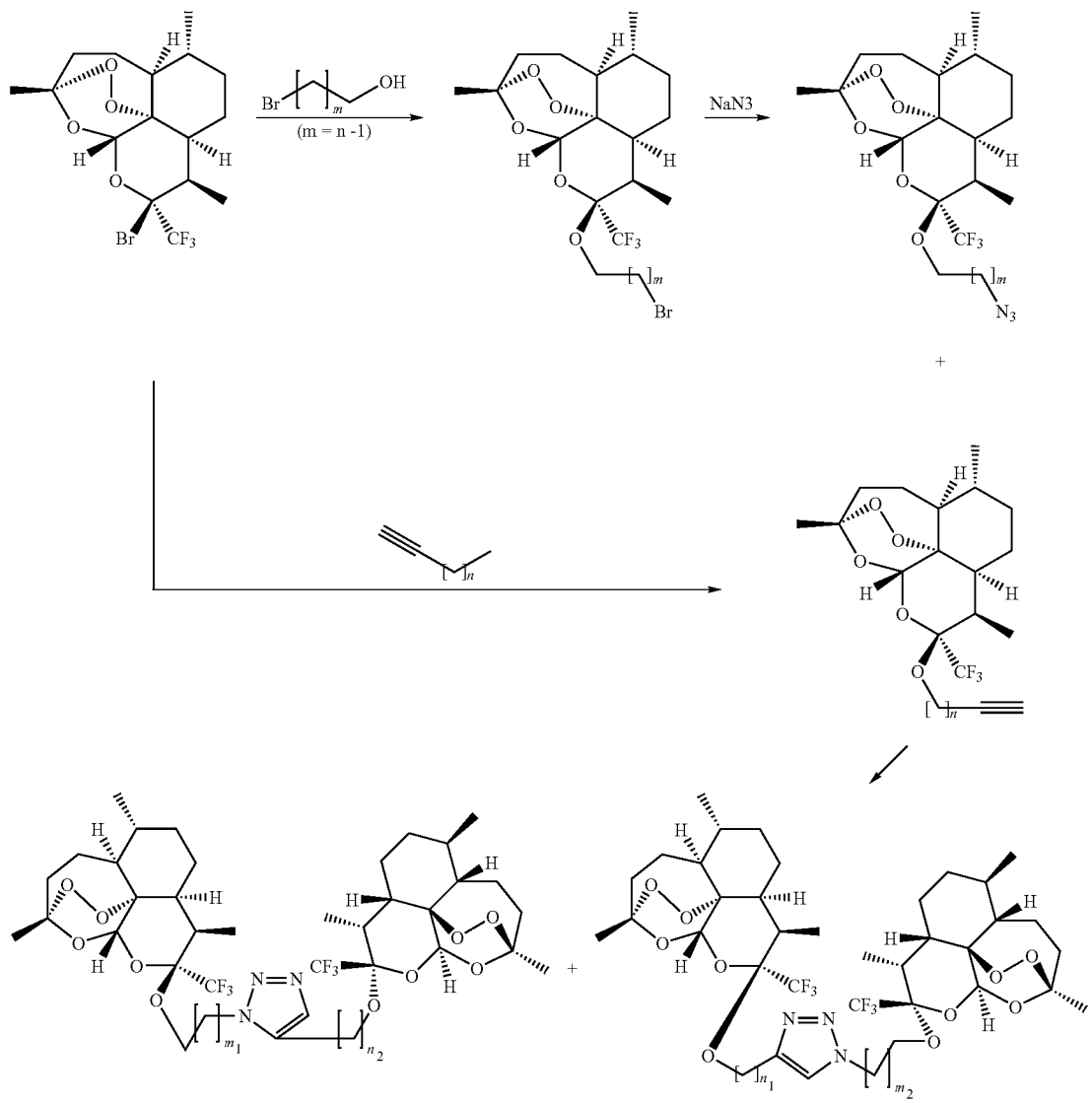

The subject of the present invention relates to a process for preparing a product of general formula (I), characterized in that the product of the following general formula (III):

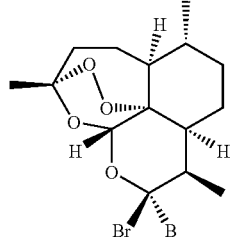

(III)

in which B represents a substituent $B_1$ or $B_2$ as defined above, undergoes a substitution of the bromine atom with the aid of a nucleophile such as a bromoalcohol, to give a product of the following general formula (II):

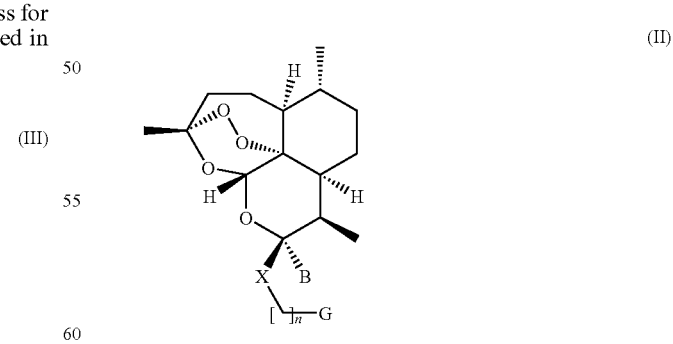

(II)

in which X represents a substituent $X_1$ or $X_2$, as defined above, n represents $n_1$ or $n_2$, as defined above, and in which either G represents a leaving group such as a bromine atom, and then this product of general formula (II) undergoes a nucleophilic substitution in order to form a dimer of general formula (I) or a precursor of a product of general formula (I), or G represents a chemical functional group F1, which may be optionally activated by a reduction or oxidation reaction, and then this product of general formula (II) reacts with another product of formula (II) where G represents a leaving group such as a bromine atom or a chemical functional group F2 capable of reacting with F1, in order to form a dimer of general formula (I) or a precursor of a product of general formula (I).

The subject of the present invention relates more particularly to the products of general formula (II) in which X is an oxygen atom, n has the value 0, 1, 2, 3 or 4, B is a trifluoromethyl group and G represents a bromine atom or an —N3, —NH2, alkenyl, alkynyl or —COOH group. These compounds are useful as intermediate products for the synthesis of the products of general formula (I).

The expression leaving group is understood to mean a group which can be easily cleaved from the molecule by breaking a heterolytic bond, with departure of an electron pair. This group may thus be easily replaced by another group during a substitution reaction for example. Such leaving groups are, for example, halogens or an activated hydroxyl group such as methanesulfonate, benzenesulfonate, p-toluenesulfonate, triflate, acetate and the like. Examples of leaving groups and references for their preparation are given in "Advances in Organic Chemistry", J. March, 3$^{rd}$ Edition, Wiley Interscience, p. 310-316.

The following examples describe the preparation of some products in accordance with the invention. These examples are not limiting and only illustrate the present invention.

Abbreviations:

° C. degrees Celsius; TLC thin layer chromatography; δ chemical shift; d doublet; dd doublet of doublets; DMSO-d$^6$ deuterated dimethyl sulfoxide; dt doublet of triplets; eq. equivalent; ES+/− electrospray (positive/negative modes); g gram; h hour; Hz hertz; IC50 inhibition constant at 50% of activity; J coupling constant; m multiplet; mg milligram; MHz megahertz; ml milliliter; μl microliter; mm millimeter; μm micrometer; mmol millimole; ppm parts per million; q quadruplet; Rf retardation factor; $^1$H NMR proton nuclear magnetic resonance; s singlet; bs broad singlet; t triplet; U.V. ultraviolet EX1: (3S,5aS,6R,8aS,9R,10R,12R,12aR,3'S,5'aS,6'R,8'aS,-9'R,10'R,12'R,12'aR)-10,10'-[thiobis(2,1-ethanediyloxy)]-bis[decahydro-3,6,9-trimethyl-10-(trifluoromethyl)-3,12-epoxy-12H-pyrano[4,3-j]-1,2-benzodioxepine

EX1

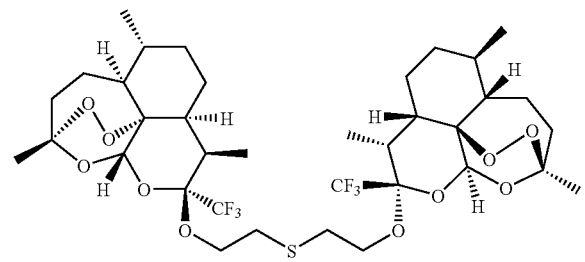

a) Step 1: Preparation of (3S,5aS,6R,8aS,9R,10R,12R,-12aR,3'S,5'aS,6'R,8'aS,9'R,10'R,12'R,12'aR)-10-(2-bromoethoxy)decahydro-3,6,9-trimethyl-10-(trifluoromethyl)-3,12-epoxy-12H-pyrano[4,3-j]-1,2-benzodioxepine 2

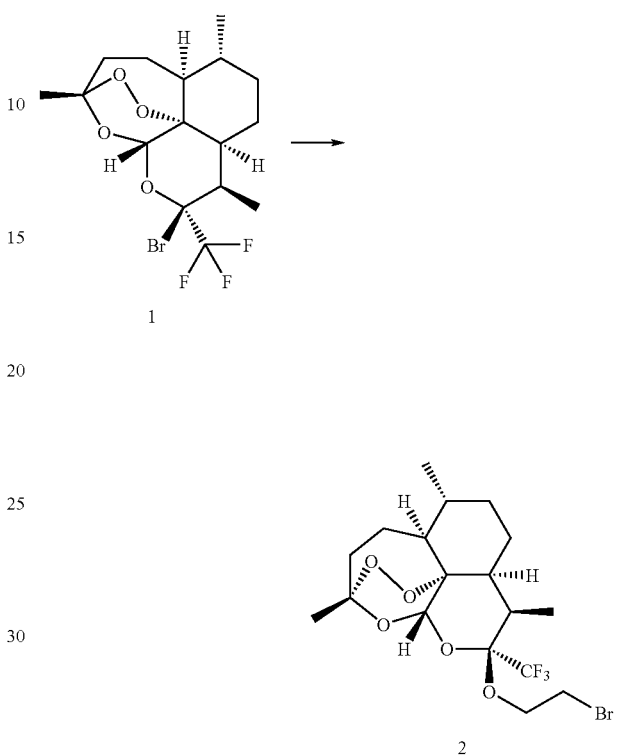

1.2 ml of hexafluoropropanol (5 eq.) and then 1.6 ml of 2-bromoethanol (10 eq.) are successively added at room temperature to a solution of 942 mg (2.27 mmol) of (3S,5aS,6R,8aS,9R,10S,12R,12aR)-10-(bromo)decahydro-3,6,9-trimethyl-10-(trifluoromethyl)-3,12-epoxy-12H-pyrano[4,3-j]-1,2-benzodioxepine 1 (prepared according to Org. Lett. 2002, 4, 757-759), in 20 ml of dichloromethane. The reaction mixture is then stirred at room temperature for 2 hours 15 minutes, and then 10 ml of a saturated sodium bicarbonate solution are added. The organic phase is dried over magnesium sulfate and evaporated to dryness under reduced pressure. The oily residue obtained is chromatographed on silica gel conditioned beforehand in heptane and then eluted with a linear gradient from 0 to 100% of the mixture B [(Heptane/Ethyl acetate), (90/10), (V/V)] in A (Heptane). 217 mg (21%) of the expected product 2 are obtained in the form of an oil.

Rf=0.45 in the system (Heptane/Ethyl acetate), (90/10), (V/V)

ES: m/z=481 (MNa$^+$)

$^1$H NMR at 400 MHz on a BRUKER AVANCE DRX-400 spectrometer with the chemical shifts (δ in ppm)—in the solvent chloroform-d1 (CDCl3-d1) referenced at 7.27 at the temperature of 303K: 0.92 (partially masked m, 1H); 0.96 (d, J=6.5 Hz, 3H); 1.01 (broad d, J=7.5 Hz, 3H); from 1.21 to 1.58 (m, 4H); 1.42 (s, 3H); from 1.65 to 2.08 (m, 5H); 2.38 (m, 1H); 2.88 (m, 1H); from 3.45 to 3.57 (m, 2H); 4.02 (m, 1H); 4.17 (m, 1H); 5.57 (s, 1H)

b) Step 2: Preparation of EX1

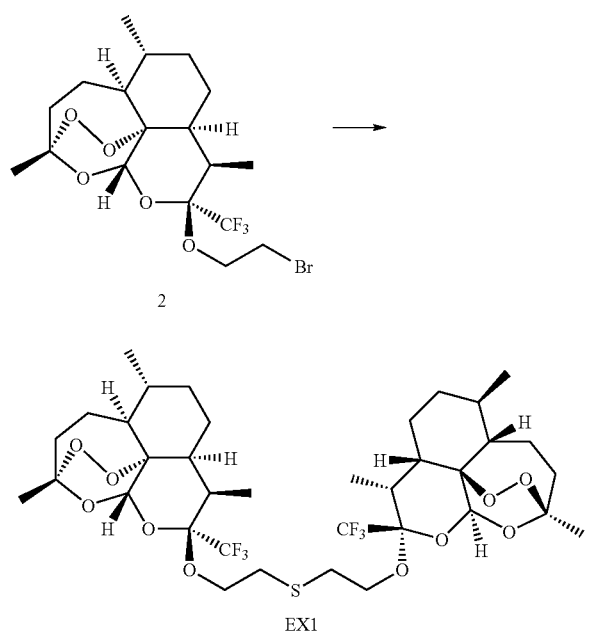

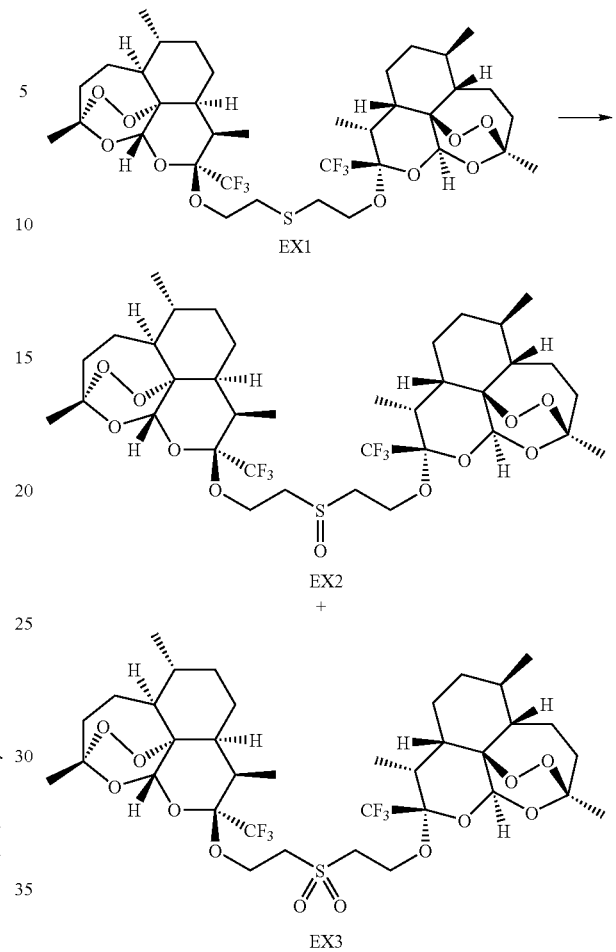

18 mg (0.234 mmol) of sodium sulfate are added, after 10 minutes, to a solution of 215 mg (0.47 mmol) of 2 in 16 ml of anhydrous ethanol, under an inert atmosphere of argon at a temperature in the region of 20° C. The stirring is maintained at this temperature for about 190 hours. 20 ml of saturated sodium chloride solution are then added. The mixture is extracted with 3×20 ml of ethyl acetate. The organic phases are combined, washed with 20 ml of a saturated NaCl solution, dried over magnesium sulfate and evaporated to dryness under reduced pressure. The oily residue obtained is chromatographed on silica gel conditioned beforehand in heptane, and then eluted with a linear gradient from 0 to 100% of the mixture B [(Heptane/Ethyl acetate), (85/15), (V/V)] in A (Heptane). 60 mg (33%) of the expected product EX1 are obtained in the form of a foam.

Rf=0.20 in the system (Heptane/Ethyl acetate), (90/10), (V/V)

ES: m/z=835 (M+HCOOH—H)$^-$ $^1$H NMR at 400 MHz on a BRUKER AVANCE DRX-400 spectrometer with the chemical shifts (δ in ppm)—in the solvent dimethyl sulfoxide-d6 (DMSO-d6) referenced at 2.50 ppm at the temperature of 303K: 0.86 (partially masked m, 2H); 0.90 (d, J=6.5 Hz, 6H); 0.93 (broad d, J=7.5 Hz, 6H); 1.22 (m, 2H); from 1.27 to 1.60 (m, 8H); 1.31 (s, 6H); 1.66 (m, 2H); from 1.75 to 1.89 (m, 4H); 2.04 (m, 2H); 2.21 (m, 2H); 2.67 (m, 2H); from 2.71 to 2.87 (m, 4H); 3.64 (m, 2H); 3.94 (m, 2H); 5.58 (s, 2H)

EX2: (3S,5aS,6R,8aS,9R,10R,12R,12aR,3'S,5'aS,6'R,8'aS,-9'R,10'R,12'R,12'aR)-10,10'-[sulfinylbis(2,1-ethanediyloxy)]bis[decahydro-3,6,9-trimethyl-10-(trifluoromethyl)-3,12-epoxy-12H-pyrano[4,3-j]-1,2-benzodioxepine and EX3: (3S,5aS,6R,8aS,9R,10R,12R,12aR,3'S,5'aS,6'R,8'aS,-9'R,10'R,12'R,12'aR)-10,10'-[sulfonylbis(2,1-ethanediyloxy)]bis[decahydro-3,6,9-trimethyl-10-tri-fluoromethyl)-3,12-epoxy-12H-pyrano[4,3-j]-1,2-benzodioxepine 16.4 mg (0.066 mmol) of meta-chloroperbenzoic acid are slowly added to a solution of 35 mg (0.044 mmol) of EX1 in 3 ml of dichloromethane at a temperature in the region of 20° C. The stirring is maintained at this temperature for about 3 hours and then 3 ml of a saturated sodium bicarbonate solution are added. The mixture is extracted with 3×10 ml of ethyl acetate. The organic phases are combined, washed with 2×10 ml of a saturated aqueous sodium chloride solution, dried over magnesium sulfate, filtered and evaporated to dryness under reduced pressure. The oily residue obtained is chromatographed on silica gel conditioned beforehand in heptane, and then eluted with a linear gradient from 0 to 100% of ethyl acetate in heptane. 14.5 mg (40%) of the product EX3 are obtained in the form of a white solid:

Rf=0.60 in the system (Heptane/Ethyl acetate), (50/50), (V/V)

ES: m/z=867 (M+HCOOH—H)$^-$ $^1$H NMR at 500 MHz on a BRUKER AVANCE DRX-500 spectrometer with the chemical shifts (δ in ppm)—in the solvent dimethyl sulfoxide-d6 (DMSO-d6) referenced at 2.50 ppm at a temperature of 298K: 0.85 (partially masked m, 2H); 0.89 (d, J=6.5 Hz, 6H); 0.92 (broad d, J=7.5 Hz, 6H); 1.18 (m, 2H); 1.32 (s, 6H); 1.36 (m, 2H); from 1.47 to 1.58 (m, 6H); 1.62 (m, 2H); 1.71 (m, 2H); 1.84 (m, 2H); 2.04 (m, 2H); 2.21 (m, 2H); 2.68 (m, 2H); 3.48 (m, 2H); 3.59 (m, 2H); 3.83 (m, 2H); 4.19 (m, 2H); 5.63 (s, 2H).

and 12.4 mg (35%) of the product EX2 in the form of a white foam:

Rf=0.22 in the system (Heptane/Ethyl acetate), (50/50), (V/V)

ES: m/z=851 (M+HCOOH—H)⁻

¹H NMR at 500 MHz on a BRUKER AVANCE DRX-500 spectrometer with the chemical shifts (δ in ppm)—in the solvent dimethyl sulfoxide-d6 (DMSO-d6) referenced at 2.50 ppm at a temperature of 298K (a 50%-50% mixture of isomers): 0.85 (partially masked m, 2H); 0.88 (d, J=6.5 Hz, 3H); 0.90 (d, J=6.5 Hz, 3H); 0.93 (broad d, J=7.5 Hz, 6H); from 1.14 to 1.89 (m, 16H); 1.31 (s, 3H); 1.32 (s, 3H); 2.03 (m, 2H); 2.20 (m, 2H); 2.67 (m, 2H); 2.98 (m, 2H); 3.12 (m, 2H); 3.79 (m, 1H); 3.87 (m, 1H); from 4.11 to 4.20 (m, 2H); 5.58 (s, 1H); 5.61 (s, 1H)

EX4: (3S,5aS,6R,8aS,9R,10R,12R,12aR,3'S,5'aS,6'R,8'aS,-9'R,10'R,12'R,12'aR)-10,10'-[thiobis(3,1-propanediyloxy)]bis[decahydro-3,6,9-trimethyl-10-(trifluoromethyl)-3,12-epoxy-12H-pyrano[4,3-j]-1,2-benzodioxepie

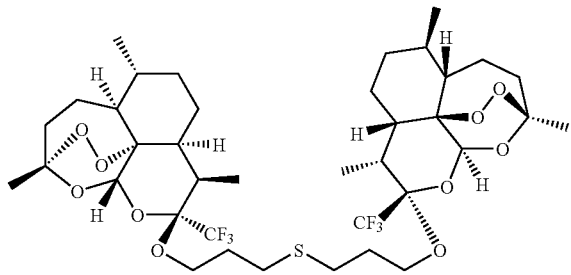

EX4 a) Step 1: Preparation of (3S,5aS,6R,8aS,9R,10R,12R,-12aR,3'S,5'aS,6'R,8'aS,9'R,10'R,12'R,12'aR)-10(3-bromopropoxy)decahydro-3,6,9-trimethyl-10-(trifluoromethyl)-3,12-epoxy-12H-pyrano[4,3-j]-1,2-benzodioxepine 3

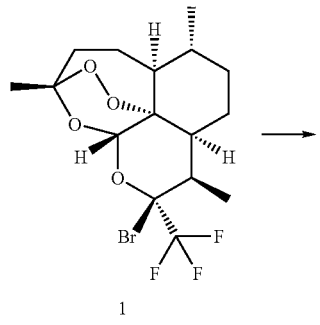

1

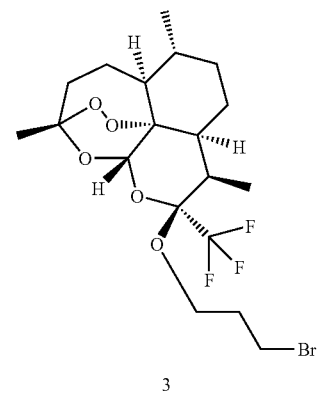

3

0.607 ml of hexafluoropropanol (5 eq.) and then 1.03 ml of 3-bromopropanol (10 eq.) are successively added at room temperature to a solution of 471 mg (1.14 mmol) of 1 in 7 ml of dichloromethane. The reaction mixture is then stirred at room temperature for 2 hours 30 minutes, and then 5 ml of a saturated sodium bicarbonate solution are added, the organic phase is dried over magnesium sulfate, filtered and evaporated to dryness under reduced pressure. The oily residue obtained is chromatographed on silica gel conditioned beforehand in heptane and then eluted with a linear gradient from 0 to 100% of the mixture B [(Heptane/Ethyl acetate), (90/10), (V/V)] in A (Heptane). 229 mg (43%) of the expected product 3 are obtained in the form of an oil.

Rf=0.38 in the system (Heptane/Ethyl acetate), (90/10), (V/V)

CI: m/z=490 (MNH₄)⁺; m/z=354 (m/z=490−BrCH₂CH₂CH₂OH+2H)⁺

¹H NMR at 400 MHz on a BRUKER AVANCE DRX-400 spectrometer with the chemical shifts (δ in ppm)—in the solvent chloroform-d1 (CDCl3-d1) referenced at 7.27 ppm at the temperature of 303K: 0.90 (partially masked m, 1H); 0.97 (d, J=6.5 Hz, 3H); 1.00 (broad d, J=7.5 Hz, 3H); from 1.22 to 1.54 (m, 4H); 1.44 (s, 3H); from 1.60 to 1.73 (m, 2H); 1.82 (m, 1H); 1.91 (m, 1H); from 2.00 to 2.20 (m, 3H); 2.39 (m, 1H); 2.87 (m, 1H); from 3.45 to 3.55 (m, 2H); 3.80 (m, 1H); 3.94 (m, 1H); 5.41 (s, 1H).

b) Step 2: preparation of EX4

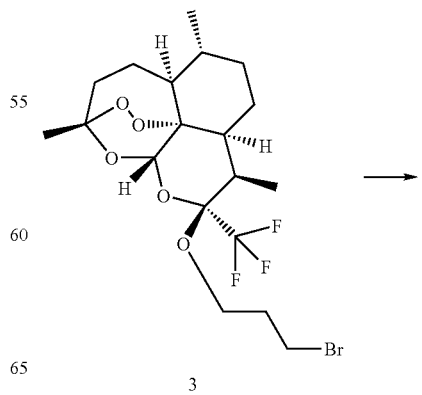

3

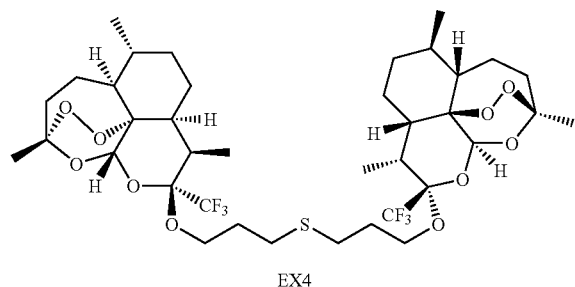

EX4

18.2 mg (0.23 mmol) of sodium sulfide are added, after 10 minutes, to a solution of 220 mg (0.46 mmol) of the product 3 in 16 ml of anhydrous ethanol, under an inert atmosphere of argon at a temperature in the region of 20° C., the stirring is maintained at this temperature for about 80 hours and then 20 ml of a saturated sodium chloride solution are added. The mixture is extracted with 3×20 ml of ethyl acetate. The organic phases are combined, washed with 20 ml of a saturated aqueous sodium chloride solution, dried over magnesium sulfate, filtered and evaporated to dryness under reduced pressure. The oily residue obtained is chromatographed on silica gel conditioned beforehand in heptane and then eluted with a linear gradient from 0 to 100% of the mixture B [(Heptane/Ethyl acetate), (85/15), (V/V)] in A (Heptane). 103 mg (54%) of the expected product EX4 are obtained in the form of a white solid.

Rf=0.20 in the system (Heptane/Ethyl acetate), (90/10), (V/V)

ES: m/z=841 MNa$^+$ $^1$H NMR at 400 MHz on a BRUKER AVANCE DRX-400 spectrometer with the chemical shifts (δ in ppm)—in the solvent chloroform-d1 (CDCl3-d1) referenced at 7.27 at the temperature of 303K: 0.93 (partially masked m, 2H); 0.97 (d, J=6.5 Hz, 6H); 1.00 (broad d, J=7.5 Hz, 6H); from 1.22 to 1.38 (m, 4H); 1.43 (s, 6H); from 1.44 to 1.55 (m, 4H); from 1.63 to 1.74 (m, 12H); 2.04 (m, 2H); 2.38 (m, 2H); from 2.51 to 2.66 (m, 4H); 2.85 (m, 2H); 3.71 (m, 2H); 3.91 (m, 2H); 5.37 (s, 2H).

EX5: (3S,5aS,6R,8aS,9R,10R,12R,12aR,3'S,5'aS,6'R,8'aS,-9'R,10'R,12'R,12'aR)-10,10'-[sulfinylbis(3,1-propane-diyloxy)]bis[decahydro-3,6,9-trimethyl-10-(trifluorom-ethyl)-3,12-epoxy-12H-pyrano[4,3-j]-1,2-benzodioxepine and EX6: (3S,5aS,6R,8aS,9R,10R,12R,12aR,3'S,5'aS,6'R,8'aS,-9'R,10'R,12'R,12'aR)-10,10'-[sulfonylbis(3,1-propane-diyloxy)]bis[decahydro-3,6,9-trimethyl-10-(trifluo-romethyl)-3,12-epoxy-12H-pyrano[4,3-j]-1,2-benzodioxepine

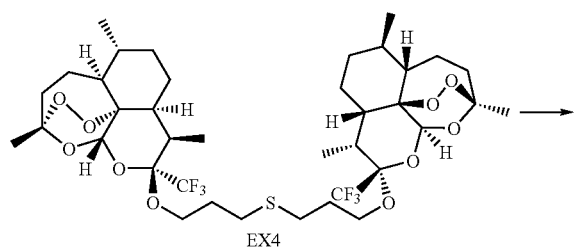

EX4

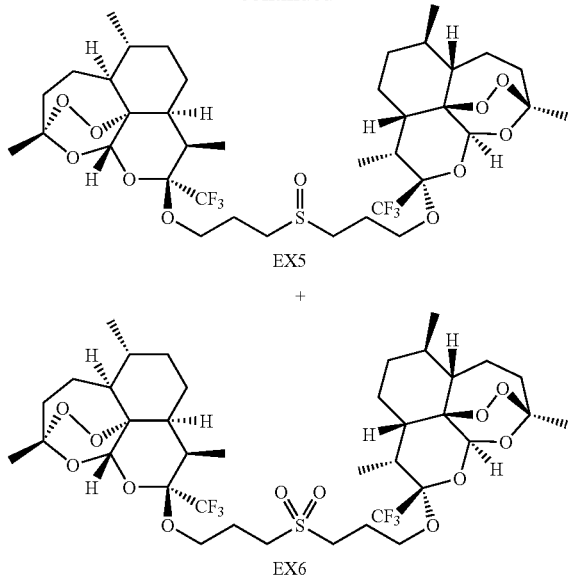

EX5

+

EX6

9.1 mg (0.036 mmol) of meta-chloroperbenzoic acid are slowly added to a solution of 21.4 mg (0.026 mmol) of EX4 in 2 ml of dichloromethane at a temperature in the region of 20° C. The stirring is maintained at this temperature for about 3 hours and then 3 ml of a saturated sodium bicarbonate solution are added. The mixture is extracted with 3×10 ml of ethyl acetate. The organic phases are combined, washed with 2×10 ml of a saturated aqueous sodium chloride solution, dried over magnesium sulfate, filtered and evaporated to dryness under reduced pressure. The oily residue obtained is chromatographed on silica gel conditioned beforehand in heptane and then eluted with a linear gradient from 0 to 100% of ethyl acetate in heptane. 7.7 mg (34%) of the product EX6 are obtained in the form of a white solid.

Rf=0.68 in the system (Heptane/Ethyl acetate), (50/50), (V/V)

ES: m/z=873 MNa$^+$ $^1$H NMR at 400 MHz on a BRUKER AVANCE DRX-400 spectrometer with the chemical shifts (δ in ppm)—in the solvent chloroform-d1 (CDCl3-d1) referenced at 7.27 at the temperature of 303K: 0.92 (partially masked m, 2H); 0.97 (d, J=6.5 Hz, 6H); 1.00 (broad d, J=7.5 Hz, 6H); from 1.23 to 1.38 (m, 4H); 1.43 (s, 6H); from 1.44 to 1.72 (m, 8H); 1.83 (m, 2H); 1.92 (m, 2H); 2.05 (m, 2H); 2.12 (m, 4H); 2.38 (m, 2H); 2.87 (m, 2H); 3.00 (m, 2H); 3.13 (m, 2H); 3.75 (m, 2H); 3.97 (m, 2H); 5.34 (s, 2H). and 8.5 mg (39%) of the product EX5 in the form of a white foam.

Rf=0.20 in the system (Heptane/Ethyl acetate), (50/50), (V/V)

ES: m/z=857 MNa$^+$ $^1$H NMR at 400 MHz on a BRUKER AVANCE DRX-400 spectrometer with the chemical shifts (δ in ppm)—in the solvent chloroform-d1 (CDCl3-d1) referenced at 7.27 at the temperature of 303K (50%-50% mixture of isomers): 0.90 (partially masked m, 2H); 0.97 (d, J=6.5 Hz, 6H); 1.00 (broad d, J=7.5 Hz, 6H); from 1.24 to 1.36 (m, 4H); 1.43 (s, 6H); from 1.45 to 1.72 (m, 8H); 1.82 (m, 2H); 1.92 (m, 2H); from 2.00 to 2.11 (m, 6H), 2.38 (m, 2H); from 2.68 to 2.82 (m, 4H); 2.86 (m, 2H); 3.77 (m, 2H); 3.96 (m, 2H); 5.33 (s, 1H); 5.35 (s, 1H).

EX7: (3S,5aS,6R,8aS,9R,10R,12R,12aR,3'S,5'aS,6'R,8'aS,-9'R,10'R,12'R,12'aR)-10,10'-[thiobis(4,1-butanediyloxy)]bis[decahydro-3,6,9-trimethyl-10-(trifluoromethyl)-3,12-epoxy-12H-pyrano[4,3-j]-1,2-benzodioxepine a) Step 1: Preparation of 3S,5aS,6R,8aS,9R,10R,12R,12aR,-3'S,5'aS,6'R,8'aS,9'R,10'R,12'R,12'aR)-10-(4-bromobutoxy)decahydro-3,6,9-trimethyl-10-(trifluoromethyl)-3,12-epoxy-12H-pyrano[4,3-j]-1,2-benzodioxepine, 4

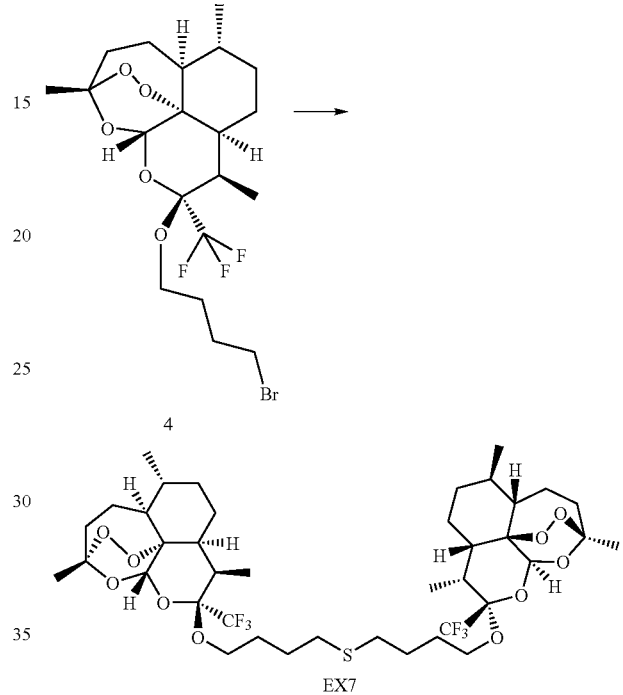

1.36 ml of hexafluoropropanol (5 eq.) and then 2.5 g of 4-bromobutanol (6.3 eq.) are successively added at room temperature to a solution of 1.07 g (2.58 mmol) of 1 in 15 ml of dichloromethane. The reaction mixture is then stirred at room temperature for 3 hours and then 6 ml of a saturated sodium bicarbonate solution. The organic phase is dried over magnesium sulfate, filtered and evaporated to dryness under reduced pressure. The oily residue obtained is chromatographed on silica gel conditioned beforehand in heptane and then eluted with a linear gradient from 0 to 100% of the mixture B [(Heptane/Ethyl acetate), (90/10), (V/V)] in A (Heptane). 90 mg (7%) of the expected product 4 are obtained in the form of an oil.

Rf=0.40 in the system (Heptane/Ethyl acetate), (9/1), (V/V)

CI: m/z=504 MNH$_4$$^+$ $^1$H NMR at 400 MHz on a BRUKER AVANCE DRX-400 spectrometer with the chemical shifts (δ in ppm)—in the solvent dimethyl sulfoxide-d6 (DMSO-d6) referenced at 2.50 ppm at the temperature of 298K: 0.92 (partially masked m, 1H); 0.97 (d, J=6.0 Hz, 3H); 1.00 (broad d, J=7.5 Hz, 3H); from 1.05 to 1.62 (partially masked m, 6H); 1.43 (s, 3H); from 1.65 to 2.10 (m, 7H); from 2.33 to 2.45 (m, 1H); 2.84 (m, 1H); from 3.40 to 3.51 (m, 2H), 3.63 (m, 1H); 3.88 (m, 1H); 5.32 (s, 1H).

b) Step 2: preparation of EX7

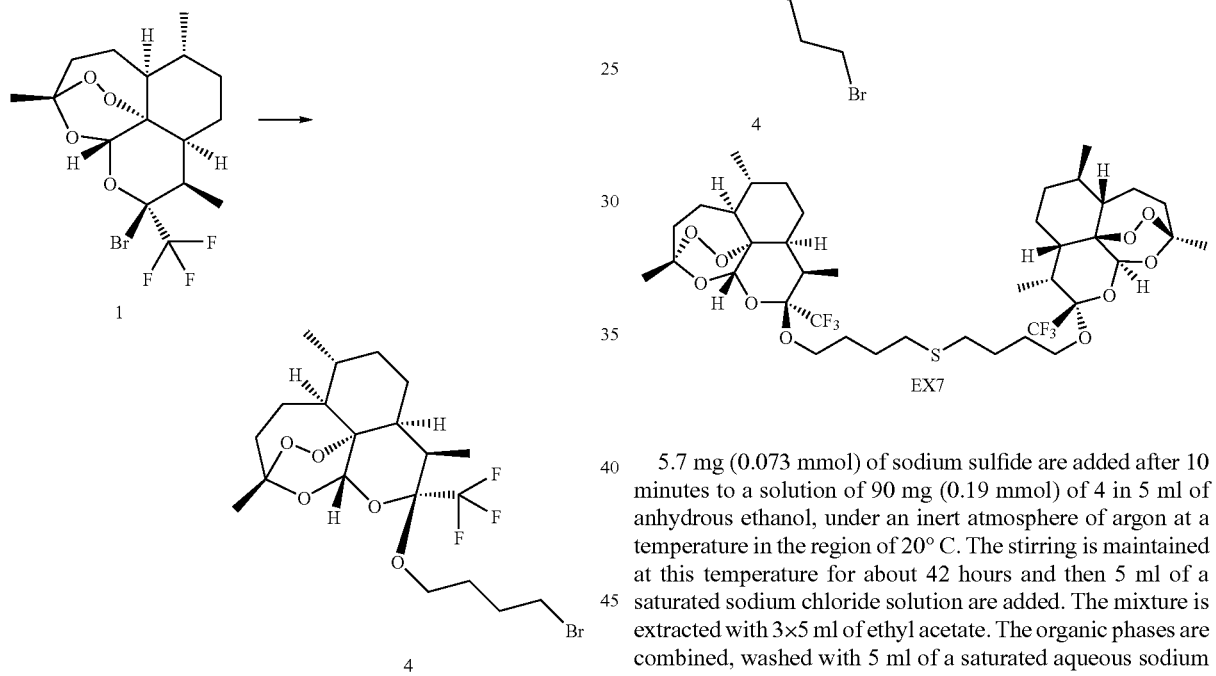

5.7 mg (0.073 mmol) of sodium sulfide are added after 10 minutes to a solution of 90 mg (0.19 mmol) of 4 in 5 ml of anhydrous ethanol, under an inert atmosphere of argon at a temperature in the region of 20° C. The stirring is maintained at this temperature for about 42 hours and then 5 ml of a saturated sodium chloride solution are added. The mixture is extracted with 3×5 ml of ethyl acetate. The organic phases are combined, washed with 5 ml of a saturated aqueous sodium chloride solution, dried over magnesium sulfate, filtered and evaporated to dryness under reduced pressure. The oily residue obtained is chromatographed on silica gel conditioned beforehand in heptane and then eluted with a linear gradient from 0 to 20% of ethyl acetate in heptane. 33 mg (50%) of the expected product EX7 are obtained in the form of a foam.

Rf=0.20 in the system (Heptane/Ethyl acetate), (9/1), (V/V)

ES: m/z=891 (M+HCOOH—H)$^-$ $^1$H NMR at 400 MHz on a BRUKER AVANCE DRX-400 spectrometer with the chemical shifts (δ in ppm)—in the solvent dimethyl sulfoxide-d6 (DMSO-d6) referenced at 2.50 ppm at the temperature of 298K: 0.93 (partially masked m, 2H); 0.97 (d, J=6.0 Hz, 6H); 1.00 (broad d, J=7.5 Hz, 6H); from 1.22 to 1.37 (m, 4H); 1.43 (s, 6H); 1.50 (m, 4H); from 1.62 to 1.86 (m, 14H); 1.91 (m, 2H); 2.04 (m, 2H); 2.38 (m, 2H); 2.54 (m, 4H); 2.84 (m, 2H); 3.62 (m, 2H); 3.85 (m, 2H); 5.33 (s, 2H).

EX8: 2-[[(3R,5aS,6R,8aS,9R,10R,12R,12aR)-decahydro-3,6,9-trimethyl-10-(trifluoromethyl)-3,12-epoxy-12H-pyrano[4,3-j]-1,2-benzodioxepin-10-yl]oxy]-N-[2-[[(3R,5aS,6R,8aS,9R,10R,12R,12aR)-decahydro-3,6,9-trimethyl-10-(trifluoromethyl)-3,12-epoxy-12H-pyrano[4,3-j]-1,2-benzodioxepin-10-yl]oxy]ethyl]-N-methylethanamine

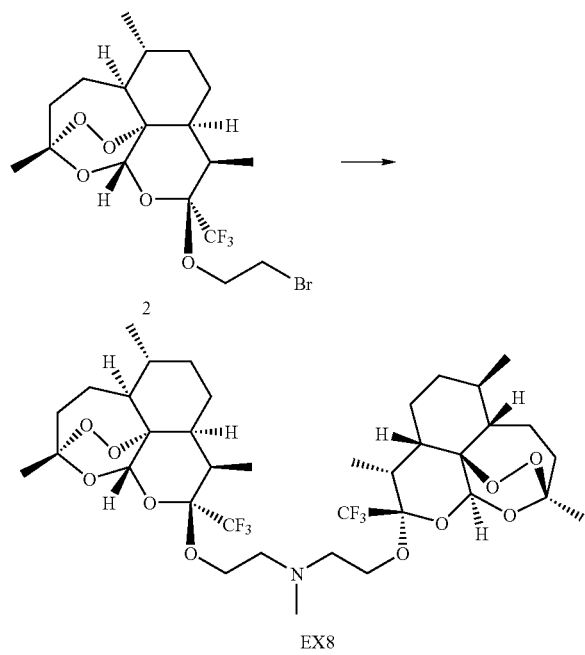

33 mg (0.218 mmol) of sodium iodide and 0.545 ml (1.09 mmol) of a 2M methylamine solution in tetrahydrofuran are successively added to a solution of 100 mg (0.218 mmol) of compound 2 in 0.6 ml of tetrahydrofuran under an inert argon atmosphere at a temperature in the region of 20° C. The stirring is maintained at 40° C. for about 20 hours. The reaction mixture is taken up in 3 ml of a saturated aqueous sodium bicarbonate solution and then extracted with 3×3 ml of dichloromethane. The organic phases are combined and then dried over magnesium sulfate, filtered and evaporated to dryness under reduced pressure. The oily residue obtained is chromatographed on silica gel conditioned beforehand in heptane and then eluted with a gradient from 0 to 30% of ethyl acetate in heptane. 15 mg (18%) of the expected product EX8 are obtained in the form of a white solid.

Rf=0.25 in the system (Heptane/Ethyl acetate), (7/3), (V/V)

ES: m/z=788 MH+

$^1$H NMR at 400 MHz on a BRUKER AVANCE DRX-400 spectrometer with the chemical shifts (δ in ppm)—in the solvent chloroform-d1 (CDCl3-d1) referenced at 7.27 at the temperature of 303K after addition of a drop of acetic acid-d4 (CD3OD-d4): 0.91 (partially masked m, 2H); 0.95 (d, J=6.5 Hz, 6H); 0.98 (broad d, J=7.0 Hz, 6H); 1.28 (m, 2H); from 1.33 to 1.63 (m, 8H); 1.39 (s, 6H); 1.69 (m, 2H); 1.78 (m, 2H); 1.89 (m, 2H); 2.02 (partially masked m, 2H); 2.36 (m, 2H); 2.86 (partially masked m, 2H); 2.89 (s, 3H); 3.38 (m, 4H); 4.19 (m, 4H); 5.38 (s, 2H).

EX 9: 2-{[[(3S,5aS,6R,8aS,9R,10R,12R,12aR)-3,6,9-trimethyl-10-(trifluoromethyl)decahydro-3,12-epoxy[1,2]dioxepino-[4,3-i]isochromen-10-yl]oxy}-N-(2-{[(3S,5aS,6R,8aS,9R,10R,12R,12aR)-3,6,9-trimethyl-10-(trifluoromethyl)decahydro-3,12-epoxy[1,2]dioxepino-[4,3-i]isochromen-10-yl]oxy}ethyl)ethanamine

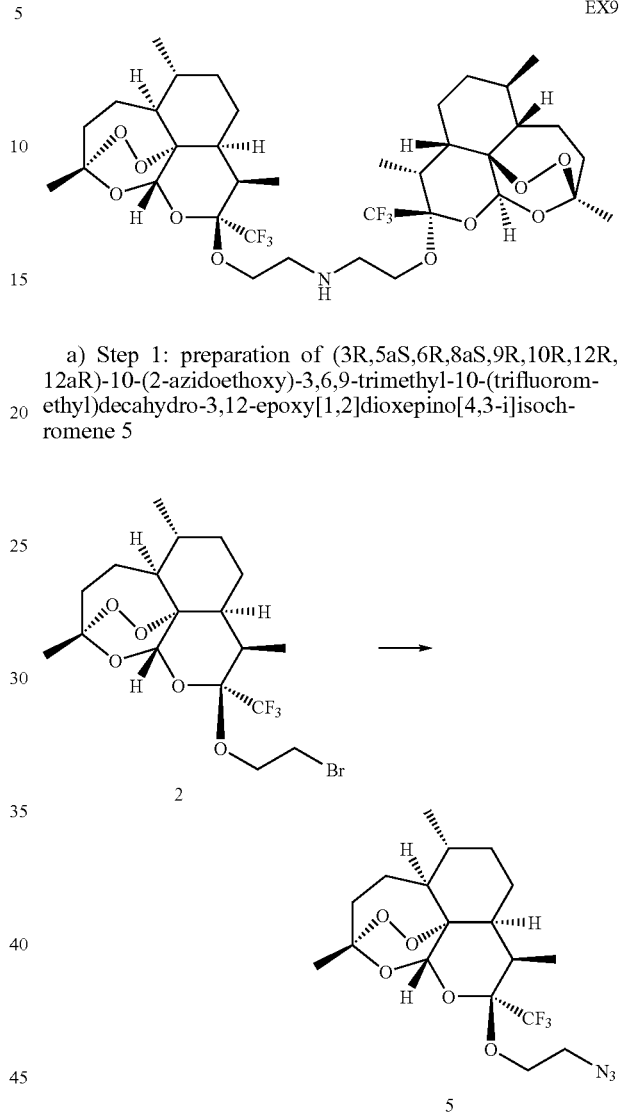

a) Step 1: preparation of (3R,5aS,6R,8aS,9R,10R,12R,12aR)-10-(2-azidoethoxy)-3,6,9-trimethyl-10-(trifluoromethyl)decahydro-3,12-epoxy[1,2]dioxepino[4,3-i]isochromene 5

162.5 mg (2.5 mmol) of sodium azide are added to a solution of 574 mg (1.25 mmol) of compound 2 in 20 ml of dimethylformamide under an inert atmosphere of argon at a temperature in the region of 20° C. The stirring is maintained at a temperature in the region of 20° C. for 3 hours. The reaction mixture is taken up in 60 ml of distilled water and then extracted with 2×100 ml of ethyl acetate. The organic phase is washed with 2×80 ml of a saturated aqueous sodium chloride solution, dried over magnesium sulfate, filtered and evaporated to dryness under reduced pressure. 527 mg (quantitative yield) of the expected product 5 are obtained in the form of a yellow oil.

Rf=0.43 in the system (Heptane/Ethyl acetate), (8/2), (V/V)

$^1$H NMR (CDCl$_3$, 400 MHz) δ$_{ppm}$: 5.48 (s, 1H); 3.97 (m, 1H); 3.78 (m, 1H); 3.48 (m, 2H); 2.88 (qu, 1H); 2.39 (td, 1H); 2.05 (dt, 1H); 1.97-1.88 (m, 1H); 1.87-1.77 (m, 2H); 1.76-1.68 (m, 1H); 1.53 (m, 1H); 1.50 (m, 1H); 1.43 (s, 3H); 1.39-1.25 (m, 2H); 1.03 (d, 3H); 1.01-0.89 (m, 1H); 0.98 (d, 3H).

b) Step 2: preparation of 2-{[(3R,5aS,6R,8aS,9R,10R, 12R,12aR)-3,6,9-trimethyl-10-(tri-fluoromethyl)decahydro-3,12-epoxy[1,2]dioxepino-[4,3-i]isochromen-10-yl]oxy) ethanamine, 6 c) Step 3: preparation of EX9

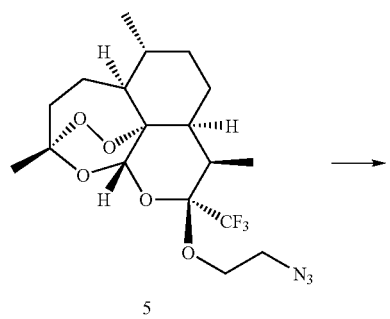

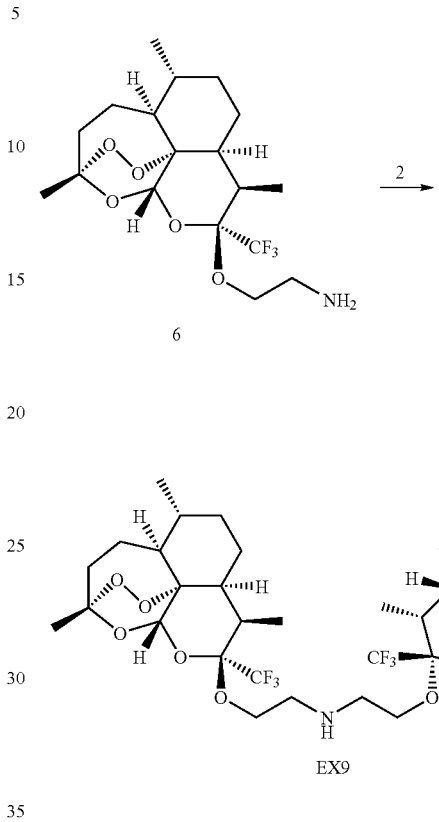

328 mg (1.25 mmol) of triphenylphosphine are added to a solution of 527 mg (1.25 mmol) of compound 5 in 7 ml of tetrahydrofuran under an inert atmosphere of argon at a temperature in the region of 20° C. The stirring is maintained at a temperature in the region of 20° C. for about 24 hours. The reaction mixture is taken up in 1 ml of distilled water and then the stirring is continued for about 24 hours at the same temperature. The reaction mixture is concentrated under vacuum and the residue thus obtained is taken up in 5 ml of dichloromethane, washed with 2 ml of a saturated aqueous sodium bicarbonate solution, dried over magnesium sulfate, filtered and evaporated to dryness under reduced pressure. The oily residue obtained is chromatographed on silica gel conditioned beforehand in dichloromethane and then eluted with a linear gradient from 0 to 100% of the mixture B [(Dichloromethane/Methanol), (90/10), (V/V)] in A (Dichloromethane). 344 mg (70%) of the expected product 6 are obtained in the form of a white powder.

MS: ES$^+$: [M+H]$^+$=396.

$^1$H NMR spectrum at 400 MHz on a BRUKER AVANCE DRX-400 spectrometer with the chemical shifts (δ in ppm)— in the solvent chloroform-d1 (CDCl3-d1) referenced at 7.27 at the temperature of 303K: 0.94 (partially masked m, 1H); 0.97 (d, J=6.5 Hz, 3H); 1.03 (broad d, J=7.0 Hz, 3H); 1.30 (m, 2H); from 1.40 to 1.56 (m, 2H); 1.42 (s, 3H); from 1.63 to 1.95 (m, 4H); 2.04 (m, 1H); 2.38 (m, 1H); 2.45 (m spread, 2H); 2.87 (m, 1H); 2.94 (m, 2H); 3.75 (m, 1H); 3.85 (m, 1H); 5.42 (s, 1H).

98 mg (0.593 mmol) of potassium iodide, 164 mg (1.19 mmol) of potassium carbonate and 232 mg (0.587 mmol) of compound 6 are successively added to a solution of 282 mg (0.534 mmol) of compound 2 in 7 ml of dimethylformamide under an inert atmosphere of argon at a temperature in the region of 20° C. The stirring is maintained at 70° C. for about 7 hours. The reaction mixture is concentrated to dryness under reduced pressure. The residue obtained is taken up in 10 ml of dichloromethane and then washed with 6 ml of distilled water, the aqueous phase is again extracted with 10 ml of dichloromethane. The combined organic phases are washed with 6 ml of a saturated aqueous sodium bicarbonate solution and then dried over magnesium sulfate, filtered and evaporated to dryness under reduced pressure. The residue obtained is chromatographed on silica gel conditioned beforehand in the mixture (Heptane/Ethyl acetate), (9/1), (V/V) and then eluted with a gradient from 10 to 60% of ethyl acetate in heptane. 116 mg (28%) of the expected product EX9 are obtained in the form of a pale yellow solid.

Rf=0.16 in the system (Heptane/Ethyl acetate), (8/2), (V/V)

MS: ES$^+$: [M+H]$^+$=774.
ES$^-$: [M+HCOOH+H]$^+$=818.

$^1$H NMR spectrum at 400 MHz on a BRUKER AVANCE DRX-400 spectrometer with the chemical shifts (δ in ppm)— in the solvent chloroform-d1 (CDCl3-d1) referenced at 7.27 at the temperature of 303K: 0.92 (partially masked m, 2H); 0.98 (d, J=6.5 Hz, 6H); 1.00 (broad d, J=7.0 Hz, 6H); from 1.20 to 1.39 (m, 4H); 1.42 (s, 6H); from 1.40 to 1.83 (m, 11H); 1.90 (m, 2H); 2.03 (m, 2H); 2.38 (m, 2H); from 2.73 to 2.91 (m, 6H); 3.75 (m, 2H); 3.91 (m, 2H); 5.47 (s, 2H).

EX 10: ethyl N,N-bis(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)glycinate

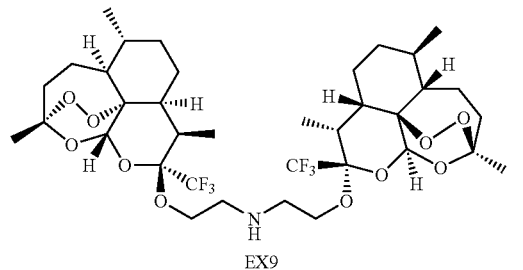

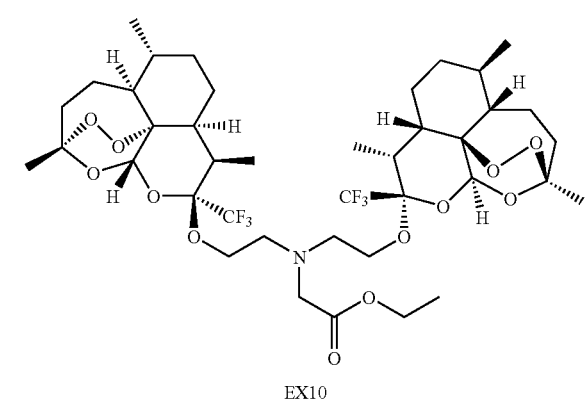

15 μl (0.133 mmol) of the ethyl ester of bromoacetic acid, 8 mg (0.047 mmol) of potassium iodide and 10 mg (0.071 mmol) of potassium carbonate are successively added to a solution of 37 mg (0.047 mmol) of the compound EX9 in 1 ml of dimethylformamide under an inert atmosphere of argon at a temperature in the region of 20° C. The stirring is maintained at 50° C. for 1 hour. The reaction mixture is concentrated to dryness under reduced pressure. The residue obtained is taken up in 5 ml of ethyl acetate and then washed with 3 ml of distilled water and the aqueous phase is again extracted with 2×5 ml of ethyl acetate. The combined organic phases are washed with 2×5 ml of a saturated aqueous sodium chloride solution and then dried over magnesium sulfate, filtered and evaporated to dryness under reduced pressure. The residue obtained is chromatographed on silica gel conditioned beforehand and then eluted in the mixture (Heptane/Ethyl acetate), (80/20), (V/V). 30 mg (74%) of the expected product EX10 are obtained in the form of a colorless paste.

TLC Rf=0.49 in the system (Heptane/Ethyl acetate), (7/3), (V/V)

MS: ES$^+$: [M+H]$^+$=860.
ES$^-$: [M+HCOOH+H]$^+$=904.

$^1$H NMR spectrum at 400 MHz on a BRUKER AVANCE DRX-400 spectrometer with the chemical shifts (δ in ppm)—in the solvent chloroform-d1 (CDCl3-d1) referenced at 7.27 at the temperature of 303K: from 0.80 to 1.00 (m, 14H); from 1.19 to 1.38 (partially masked m, 4H); 1.28 (t, J=7.0 Hz, 3H); 1.40 (s, 6H); from 1.44 to 1.58 (partially masked m, 4H); from 1.61 to 1.82 (m, 6H); 1.89 (m, 2H); 2.02 (m, 2H); 2.36 (m, 2H); from 2.70 to 2.90 (m, 4H); 3.02 (m, 2H); 3.40 (d, J=17.5 Hz, 1H); 3.61 (m, 2H); 3.67 (d, J=17.5 Hz, 1H); 3.98 (m, 2H); from 4.06 to 4.22 (m, 2H); 5.40 (s, 2H).

EX 11: N,N-bis(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochomen-10-yl]oxy}ethyl)glycine

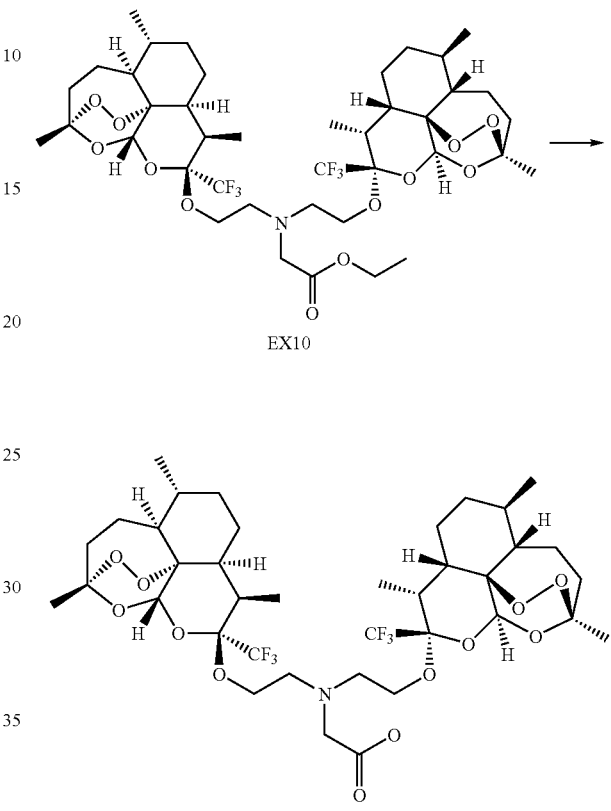

59 μl (0.059 mmol) of a 1N aqueous sodium hydroxide solution are added to a solution of 10 mg (0.011 mmol) of the compound EX10 in 0.5 ml of methanol at a temperature in the region of 20° C. The stirring is maintained at the same temperature for about 6.5 hours. The reaction mixture is concentrated to dryness under reduced pressure. The residue obtained is taken up in 3 ml of ethyl acetate and then washed with 1 ml of a saturated aqueous sodium chloride solution. The aqueous phase is again extracted with 3 ml of ethyl acetate. The combined organic phases are dried over magnesium sulfate, filtered and evaporated to dryness under reduced pressure. The residue obtained is chromatographed on silica gel conditioned beforehand and then eluted in the mixture (Dichloromethane/Methanol), (95/05), (V/V). 8 mg (81%) of the expected product EX11 are obtained in the form of a colorless solid.

MS: ES$^+$: [M+H]$^+$=832
ES$^-$: [M−H]$^-$=830.

$^1$H NMR spectrum at 300 MHz on a BRUKER AVANCE DRX-400 spectrometer with the chemical shifts (δ in ppm)—in the solvent chloroform-d1 (CDCl3-d1) referenced at 7.27 at the temperature of 303K: 0.92 (partially masked m, 2H); 0.97 (d, J=6.5 Hz, 6H); 1.01 (broad d, J=7.0 Hz, 6H); from 1.20 to 1.38 (partially masked m, 4H); 1.42 (s, 6H); from 1.44 to 1.75 (m, 8H); from 1.80 to 2.10 (m, 6H); 2.39 (m, 2H); from 2.80 to 3.02 (m, 6H); 3.38 (d, J=17.5 Hz, 1H); 3.55 (d, J=17.5 Hz, 1H); from 3.77 to 3.98 (m, 4H); 5.32 (s, 2H).

EX 12: 2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}-N-(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)acetamide

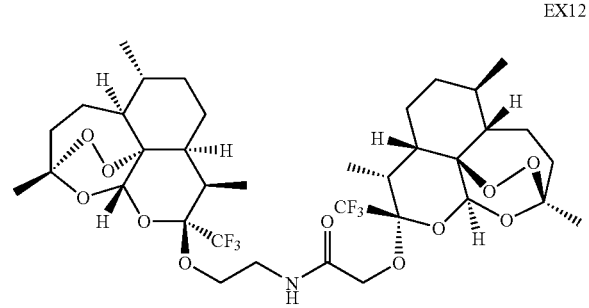

a) Step 1: preparation of {[(3R,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)acetic acid, 8

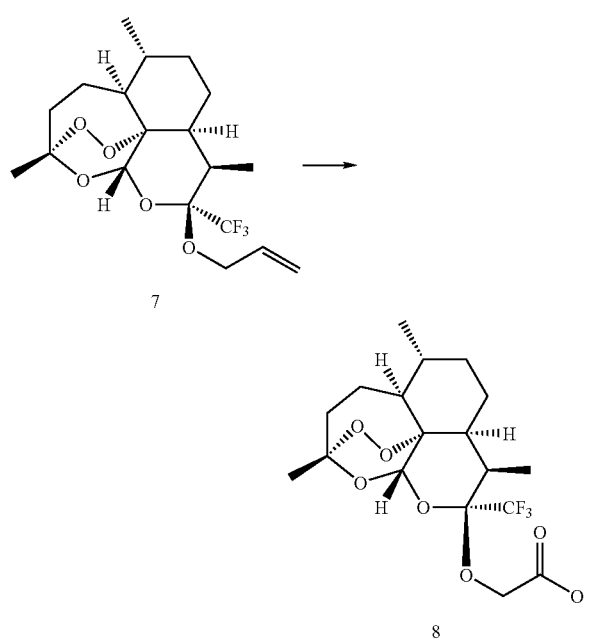

117 mg (0.742 mmol) of potassium permanganate and then 11 mg (0.127 mmol) of sodium bicarbonate are successively added at room temperature to a solution of 100 mg (0.255 mmol) of 7 (prepared according to WO2003035651), in 2 ml of acetone. The reaction mixture is then stirred at room temperature for 3 hours and then 1 eq. of a 1N aqueous hydrochloric acid solution are added. The stirring is continued at room temperature for about 18 hours. The reaction medium is filtered and then evaporated to dryness under reduced pressure. The residue obtained is taken up in 10 ml of ethyl acetate. The organic phase is washed with 3 ml of distilled water, the aqueous phase is acidified with 2 ml of a 1N aqueous hydrochloric acid solution and then extracted with 10 ml of ethyl acetate. The organic phase is dried over magnesium sulfate, filtered and then evaporated to dryness under reduced pressure. 27 mg (26%) of the expected product 8 are obtained in the form of a white solid.

$^1$H NMR (CDCl$_3$, 300 MHz) $\delta_{ppm}$: 5.47 (s, 1H); 4.67 (d, 1H); 4.26 (d, 1H); 2.91 (qu, 1H); 2.38 (td, 1H); 2.19 (dq, 1H); 2.04 (dt, 1H); 1.90 (m, 1H); 1.77 (m, 2H); 1.70 (m, 1H); 1.59-1.48 (m, 1H); 1.48-1.45 (m, 1H); 1.42 (s, 3H); 1.40-1.24 (m, 2H); 1.05 (d, 3H); 0.98-0.87 (m, 1H); 0.96 (d, 3H)

b) Step 2: preparation of EX12

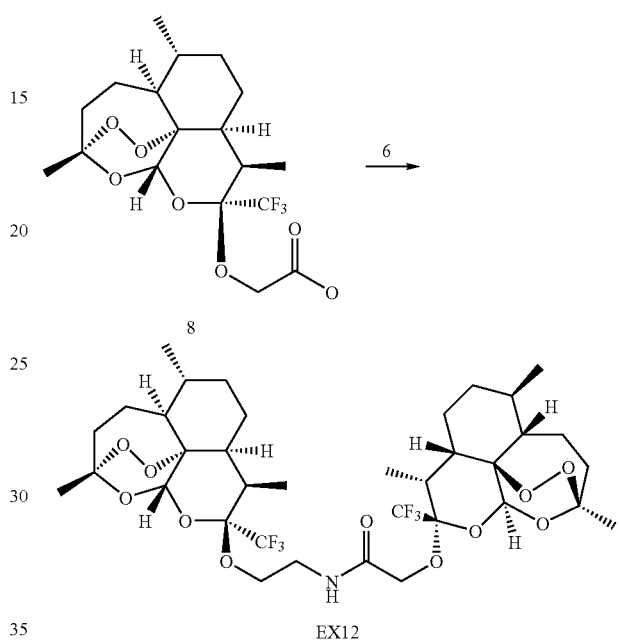

36 mg (0.27 mmol) of hydroxybenzotriazole and 52 mg (0.27 mmol) of 1-(3-dimethylaminopropyl)-3-ethylcarbodiimide hydrochloride are successively added to a solution of 37 mg (0.09 mmol) of the compound 8 in 3 ml of dichloromethane under an inert atmosphere of argon at a temperature in the region of 20° C. The stirring is maintained at a temperature in the region of 20° C. for about 30 minutes and then 39 mg (0.099 mmol) of the compound 6 are added. The stirring is continued at this temperature for 1 hour. The reaction mixture is taken up in 5 ml of distilled water and then extracted with 3×20 ml of ethyl acetate. The organic phase is washed with 2×10 ml of a saturated aqueous sodium chloride solution, dried over magnesium sulfate, filtered and evaporated to dryness under reduced pressure. The residue obtained is chromatographed on silica gel conditioned beforehand in the mixture (Heptane/Ethyl acetate), (90/10), (V/V) and then eluted with a gradient from 10 to 20% of ethyl acetate in heptane. 40 mg (56%) of the expected product EX12 are obtained in the form of a viscous gum.

MS: ES$^+$: [M+H]$^+$=788; [M+Na]$^+$=810

ES$^-$: [M−H]$^-$=786; [M+HCOOH+H]$^+$=832.

$^1$H NMR spectrum at 400 MHz on a BRUKER AVANCE DRX-400 spectrometer with the chemical shifts ($\delta$ in ppm)—in the solvent chloroform-d1 (CDCl3-d1) referenced at 7.27 at the temperature of 303K: from 0.87 to 1.03 (m, 11H); 1.08 (broad d, 3H); from 1.21 to 1.40 (m, 4H); 1.43 (s, 6H); from 1.45 to 1.65 (partially masked m, 6H); 1.69 (m, 2H); from 1.78 to 1.97 (m, 4H); 2.05 (m, 2H); from 2.32 to 2.43 (partially masked m, 2H); from 2.82 to 2.98 (m, 2H); 3.37 (m, 1H); from 3.65 to 3.81 (m, 2H); 3.95 (m, 1H); 4.14 (d, J=16.0 Hz, 1H); 4.43 (d, J=16.0 Hz, 1H); 5.33 (s, 1H); 5.36 (s, 1H); 6.52 (m, 1H).

EX 13: (3S,5aS,6R,8aS,9R,10R,12R,12aR,3'S,5'aS,6'R, 8'aS,-9'R,10'R,12'R,12'aR)-10,10'-[(2E)-but-2-ene-1,4-diyl-bis(oxy)]bis[3,6,9-trimethyl-10-(trifluoromethyl)decahydro-3,12-epoxy[1,2]dioxepino[4,3-i]isochromene] and EX14: (3S,5aS,6R,8aS,9R,10R,12R,12aR,3'S,5'aS,6'R, 8'aS,-9'R,10'R,12'R,12'aR)-10,10'-[(2Z)-but-2-ene-1,4-diyl-bis(oxy)]bis[3,6,9-trimethyl-10-(trifluoromethyl)decahydro-3,12-epoxy[1,2]dioxepino[4,3-i]isochromene]

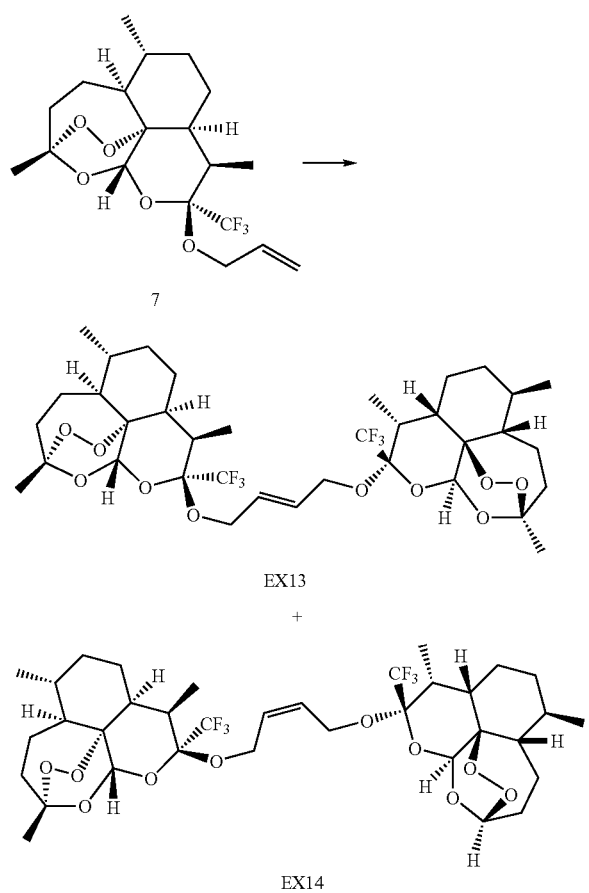

A suspension of 200 mg (0.51 mmol) of the compound 7 and 43 mg (0.051 mmol) of benzylidenebis(tricyclohexylphosphine)dichlororuthenium in 1.3 ml of dichloromethane is stirred for about 7 hours at a temperature in the region of 20° C. A solution containing 633 mg (5.10 mmol) of trishydroxymethylphosphine and 1.43 ml (10.2 mmol) of triethylamine in 3 ml of dichloromethane is added. Vigorous stirring is maintained at a temperature in the region of 20° C. for about 10 minutes and then 6 ml of water are added, the stirring is continued for 1 hour. The organic phase is washed with 3 ml of distilled water, dried over magnesium sulfate, filtered and evaporated to dryness under reduced pressure. The oily residue obtained is chromatographed on silica gel conditioned beforehand and then eluted in the mixture (Heptane/Ethyl acetate), (95/5), (V/V). 57.5 mg (38%) of the E isomer EX13 are obtained in the form of white crystals. 20 mg (10%) of the Z isomer EX14 are obtained in the form of white crystals.

EX13:
Rf=0.41 in the system (Heptane/Ethyl acetate), (8/2), (V/V)
IR: 983 cm$^{-1}$ (characteristic trans CH=CH band).
MS: ES$^+$: [M+Na]$^+$=779.
ES$^-$: [M+HCOOH+H]$^+$=801.
$^1$H NMR (CDCl$_3$, 300 MHz) $\delta_{ppm}$: 5.79 (t, 2H); 5.32 (s, 2H); 4.37 (dd, 2H); 4.19 (dd, 2H); 2.87 (qu, 2H); 2.39 (td, 2H); 2.04 (dt, 2H); 1.97-1.87 (m, 2H); 1.85-1.75 (m, 2H); 1.75-1.62 (m, 4H); 1.57-1.49 (m, 2H); 1.47 (m, 2H); 1.43 (s, 6H); 1.37-1.20 (m, 4H); 1.02 (d, 6H); 1.00-0.84 (m, 2H); 0.97 (d, 6H).
EX14:
Rf=0.47 in the system (Heptane/Ethyl acetate), (8/2), (V/V)
MS: ES$^+$: [M+NH$_4$]$^+$=774.
$^1$H NMR (CDCl$_3$, 300 MHz) $\delta_{ppm}$: 5.67 (t, 2H); 5.31 (s, 2H); 4.42 (dd, 2H); 4.25 (dd, 2H); 2.85 (qu, 2H); 2.38 (td, 2H); 2.04 (dt, 2H); 1.96-1.84 (m, 2H); 1.84-1.74 (m, 2H); 1.74-1.61 (m, 4H); 1.57-1.49 (m, 2H); 1.47 (m, 2H); 1.43 (s, 6H); 1.37-1.20 (m, 4H); 1.01 (d, 6H); 1.00-0.87 (m, 2H); 0.97 (d, 6H).
EX15: (3S,5aS,6R,8aS,9R,10R,12R,12aR,3'S,5'aS,6'R, 8'aS,-9'R,10'R,12'R,12'aR)-10,10'-[(2R,3R)-oxirane-2,3-diylbis(methyleneoxy)]bis[3,6,9-trimethyl-10-(trifluoromethyl)-decahydro-3,12-epoxy[1,2]dioxepino[4,3-i] isochromene]

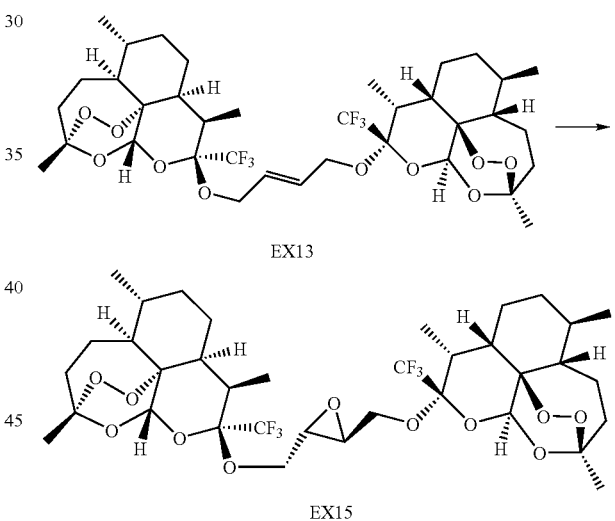

103 mg (0.417 mmol) of meta-chloroperbenzoic acid are added to a solution of 158 mg (0.209 mmol) of the compound EX13 in 2.75 ml of dichloromethane at a temperature in the region of 20° C. The stirring is maintained at this temperature for about 8 hours. The reaction mixture is successively washed with 3×5 ml of a saturated aqueous sodium bicarbonate solution and 13 ml of a saturated aqueous sodium chloride solution. The organic phase is dried over magnesium sulfate, filtered and evaporated to dryness under reduced pressure. The oily residue obtained is chromatographed on silica gel conditioned beforehand and then eluted in the mixture (Heptane/Ethyl acetate), (95/5), (V/V). 70 mg (43%) of one of the two trans isomers EX15 are obtained in the form of white crystals.

MS: ES$^+$: [M+Na]$^+$=795.
$^1$H NMR spectrum at 400 MHz on a BRUKER AVANCE DRX-400 spectrometer with the chemical shifts ($\delta$ in ppm)— in the solvent chloroform-d1 (CDCl3-d1) referenced at 7.27 at the temperature of 303K: from 0.86 to 0.98 (m, 14H); from 1.20 to 1.39 (m, 4H); 1.42 (s, 6H); from 1.44 to 1.55 (m, 4H); from 1.62 to 1.77 (m, 6H); 1.89 (m, 2H); 2.04 (m, 2H); 2.37 (m, 2H); 2.85 (m, 2H); 3.11 (broad s, 2H); 3.69 (broad d, J=12.5 Hz, 2H); 4.31 (d, J=12.5 Hz, 2H); 5.39 (s, 2H).

EX 16: (1-(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)-4-({[(3S,5aS,6R,8aS,9R,10R,-12R,12aR)-3,6,9-trimethyl-10-(trifluoromethyl)decahydro-3,12-epoxy[1,2]dioxepino[4,3-i]isochromen-10-yl]oxy}methyl)-1H-1,2,3-triazole and EX17: (1-(2-{[(3S,5aS,6R,8aS,9R,10R,-12R,12aR)-3,6,9-trimethyl-10-(trifluoromethyl)decahydro-3,12-epoxy[1,2]dioxepino[4,3-i]isochromen-10-yl]oxy}ethyl)-5-({[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)-1H-1,2,3-triazole EX16
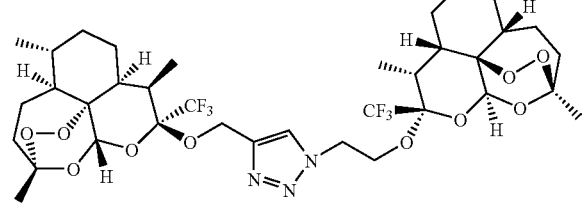

EX17
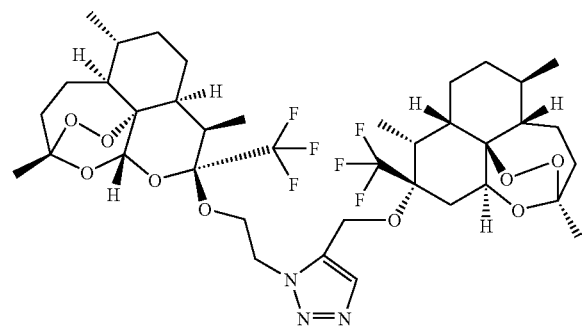

a) Step 1: preparation of (3R,5aS,6R,8aS,9R,10R,12R,12aR)-3,6,9-trimethyl-10-(prop-2-yn-1-yloxy)-10-(trifluoromethyl)decahydro-3,12-epoxy[1,2]dioxepino[4,3-i]isochromene, 9

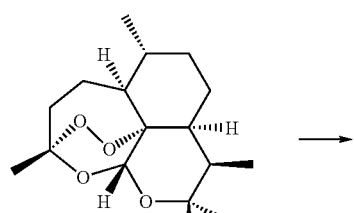

1

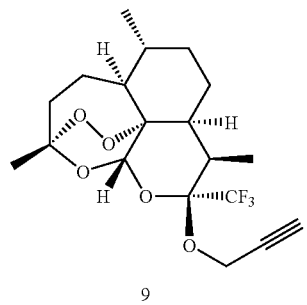

9

0.266 ml of hexafluoropropanol (5 eq.) and then 0.289 ml of propargyl alcohol (10 eq.) are successively added at room temperature to a solution of 0.206 g (0.5 mmol) of (3S,5aS,6R,8aS,9R,10S,12R,12aR)-10-(bromo)decahydro-3,6,9-trimethyl-10-(trifluoromethyl)-3,12-epoxy-12H-pyrano[4,3-j]-1,2-benzodioxepine 1

(prepared according to Org. Lett. 2002, 4, 757-759) in 5 ml of dichloromethane. The reaction mixture is then stirred at room temperature for 1 hour 15 minutes and then 5 ml of a saturated sodium bicarbonate solution are added. The organic phase is dried over magnesium sulfate and evaporated to dryness under reduced pressure. The oily residue obtained is chromatographed on silica gel conditioned beforehand in heptane and then eluted with a linear gradient from 0 to 50% of ethyl acetate in heptane. 0.064 g (34%) of the expected product 9 are obtained in the form of an oil.

Rf=0.40 in the system (Heptane/Ethyl acetate), (85/15), (V/V)

ES m/z=391 MH+ m/z=335 MH+—C3H4O

1H NMR spectrum at 400 MHz on a BRUKER AVANCE DRX-400 spectrometer with the chemical shifts (δ in ppm)— in the solvent dimethyl sulfoxide-d6 (DMSO-d6) referenced at 2.50 ppm at the temperature of 303K: 0.88 (partially masked m, 1H); 0.91 (d, J=6.5 Hz, 3H); 0.95 (broad d, J=7.5 Hz, 3H); 1.23 (m, 1H); from 1.28 to 1.43 (m, 2H); 1.32 (s, 3H); from 1.50 to 1.63 (m, 2H); from 1.73 to 1.90 (m, 3H); 2.03 (m, 1H); 2.21 (m, 1H); 2.68 (m, 1H); 3.52 (t, J=2.5 Hz, 1H); 4.30 (dd, J=2.5 and 16.0 Hz, 1H); 4.51 (dd, J=2.5 and 16.0 Hz, 1H); 5.57 (s, 1H).

b) Step 2: preparation of EX16 and EX17

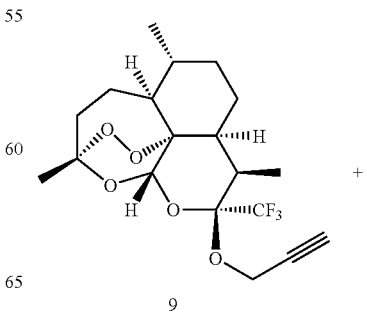

9

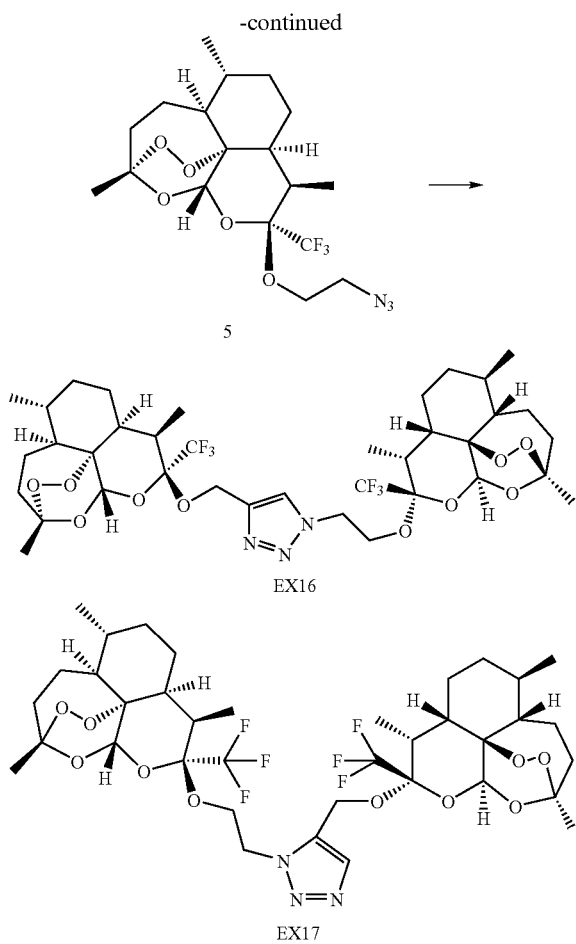

257 mg (0.610 mmol) of compound 5 are added to a solution of 119 mg (0.305 mmol) of the compound 9 in 2.5 ml of ethanol at a temperature in the region of 20° C. The stirring is maintained under reflux for about 48 hours. The reaction mixture is evaporated to dryness in a rotavapor and the oily residue obtained is chromatographed on silica gel conditioned beforehand in dichloromethane and then eluted with a linear gradient from 0 to 100% of the mixture B [(Dichloromethane/Ethyl acetate), (96/4), (V/V)] in A (Dichloromethane). 43 mg (18%) of the expected product EX16 are obtained in the form of a white solid and 17 mg (7%) of the expected product EX17 are obtained in the form of a white solid.

EX16:

Rf=0.26 in the system (Dichloromethane/Ethyl acetate), (96/4), (V/V).

ES m/z=834 MNa$^+$ m/z=812 MH$^+$ $^1$H NMR spectrum at 400 MHz on a BRUKER AVANCE DRX-400 spectrometer with the chemical shifts (δ in ppm)— in the solvent chloroform-d1 (CDCl3-d1) referenced at 7.27 at the temperature of 303K: from 0.75 to 1.70 (partially masked m, 16H); 0.92 (broad d, J=7.0 Hz, 9H); 0.98 (broad d, J=7.0 Hz, 3H); 1.41 (s, 3H); 1.43 (s, 3H); 1.89 (m, 2H); 2.03 (m, 2H); 2.37 (m, 2H); 2.84 (m, 2H); 4.11 (m, 1H); 4.32 (m, 1H); from 4.40 to 4.60 (m, 2H); 4.71 (d, J=12.5 Hz, 1H); 5.04 (d, J=12.5 Hz, 1H); 5.20 (s, 1H); 5.70 (s, 1H); 7.53 (s, 1H).

EX17:

TLC Rf=0.32 in the system (dichloromethane/ethyl acetate), (96/4), (V/V)

ES m/z=834 MNa$^+$ m/z=812 MH$^+$ $^1$H NMR spectrum at 500 MHz on a BRUKER AVANCE DRX-500 spectrometer with the chemical shifts (δ in ppm)— in the solvent chloroform-d1 (CDCl3-d1) referenced at 7.27 at the temperature of 303K: from 0.55 to 1.70 (partially masked m, 16H); 0.90 (broad d, J=7.0 Hz, 9H); 1.01 (broad d, J=7.0 Hz, 3H); 1.39 (s, 3H); 1.44 (s, 3H); from 2.30 to 2.43 (m, 2H); from 1.97 to 2.09 (m, 2H); from 2.28 to 2.42 (m, 2H); 2.80 (m, 1H); 2.90 (m, 1H); 4.11 (m, 1H); from 4.42 to 4.63 (m, 3H); 4.40 (d, J=13.0 Hz, 1H); 5.04 (d, J=13.0 Hz, 1H); 5.11 (s, 1H); 5.24 (s, 1H); 7.61 (s, 1H).

Antiproliferative Activity of the Products Prepared:

The products according to the invention have been the subject of pharmacological trials which make it possible to determine their antiproliferative activity. It was determined by measuring the inhibition of cell proliferation of HCT116 cells. The cells are inoculated in a cell culture medium at a concentration of 10 000 cells per well, in 0.17 ml of medium, and 20 μl of test product, at various concentrations, and 10 μl of Thymidine [methyl-14C] (100 μCi/ml—specific activity 47.90 mCi/mmol; NEN Technologies reference NEC568 batch 3550-001) are added, and then the cells are incubated at 37° C. and 5% $CO_2$.

Medium used for the culture of HCT116 cells: DMEM medium 2 mM L-glutamine, 200 IU/ml penicillin, 200 μg/ml streptomycin and 10% (V/V) fetal calf serum (Life Technologies).

After 96 hours, the incorporation of $^{14}$C-thymidine is counted in a liquid scintillation counter 1450 Microbeta Wallac Trilux. The results R are expressed in cpm (counts per minute) and converted to percentage of growth inhibition GI % by first subtracting the mean of the number of cpm of the wells without cells B and then by dividing by the number of cpm of the wells of the untreated cells C comprising 20 μl of medium for dilution of the product containing 1% of ethanol (GI %=(R−B)×100/C %).

The IC50 values are calculated with the aid of the equation 205 of the XLFit software (IDBS company, UK) by nonlinear regression analysis using the Marquardt algorithm (Donald W. MARQUARDT, J. Soc. industry appl., vol. 11, No. 2, June, 1963).

The products have an IC50 on the HCT116 cells generally of less than 10 μM and preferably of less than 100 nM.

| Examples | IC50 (nM)/HCT116 |
| --- | --- |
| EX1 | 47 |
| EX2 | 23 |
| EX3 | 21 |
| EX8 | 30 |

The products according to the invention may therefore be used for the preparation of medicaments.

Thus, according to another of its aspects, the subject of the invention is medicaments comprising a product of formula (I) or an addition salt of the latter with a pharmaceutically acceptable acid, or a hydrate or a solvate.

These medicaments find use in therapy, especially in the treatment of cancer.

The present invention therefore relates to the use of a product of formula (I) for the manufacture of a medicament useful for treating a pathological condition and more particularly the use of a product of formula (I) for the manufacture of a medicament useful for treating cancer.

The present invention also relates to the use of a product of formula (I) for the manufacture of a medicament useful for treating pathologies where new vascularization or angiogenesis occurs inappropriately, that is to say in cancers in general but also in specific cancers such as Kaposi's sarcoma or infantile hemoangioma, and also in rheumatoid arthritis, osteoarthritis and/or its associated pains, and inflammatory bowel diseases such as hemorrhagic rectocolitis or Crohn's disease, eye diseases such as age-related macular degeneration, diabetic retinopathies, chronic inflammation and psoriasis.

Angiogenesis is a process of generation of new capillary vessels from preexisting vessels. Tumor angiogenesis (formation of blood neovessels), essential for tumor growth, is also one of the main factors in metastatic dissemination (Oncogene. 2003 May 19; 22(20): 3172-9; Nat. Med. 1995 January; 1(1): 27-31).

According to another of its aspects, the present invention relates to pharmaceutical compositions comprising, as active ingredient, a product according to the invention. These pharmaceutical compositions contain an effective dose of at least one product according to the invention or a pharmaceutically acceptable salt, a hydrate or a solvate of the said product, and at least one pharmaceutically acceptable excipient.

The said excipients are chosen according to their pharmaceutical dosage form and the desired mode of administration from the usual excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, solvate or hydrate, may be administered in unit form, as a mixture with conventional pharmaceutical excipients, to animals and to human beings for the prophylaxis or treatment of the above disorders or diseases.

The appropriate unit forms for administration comprise the forms for administration by the oral route such as tablets, soft or hard gelatin capsules, powders, granules and oral solutions or suspensions, the forms for sublingual, buccal, intratracheal, intraocular or intranasal administration, the forms for administration by inhalation, the forms for topical, transdermal, subcutaneous, intramuscular or intravenous administration, the forms for rectal administration or implants. For topical application, the products according to the invention may be used in creams, gels, ointments or lotions.

By way of example, a unit form for administration of a product according to the invention in tablet form may comprise the following components:

| | |
|---|---|
| Product according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

There may be particular cases where higher or lower dosages are appropriate: such dosages do not depart from the scope of the invention. According to the usual practice, the dosage appropriate to each patient is determined by the doctor according to the mode of administration, the weight and the response of the said patient.

The present invention, according to another of its aspects, also relates to a method of treating the pathologies indicated above which comprises the administration, to a patient, of an effective dose of a product according to the invention or one of its pharmaceutically acceptable salts or its hydrates or solvates.

The products of the present invention may be administered alone or as a mixture with other anticancer agents. Among the possible combinations, there may be mentioned:
- alkylating agents, and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine
- platinum derivatives such as in particular cisplatin, carboplatin or oxaliplatin
- antibiotic agents such as in particular bleomycin, mitomycin, dactinomycin
- antimicrotubule agents such as in particular vinblastine, vincristine, vindesine, vinorelbine, taxoids (paclitaxel and docetaxel)
- anthracyclines such as in particular doxorubicin, daunorubicin, idarubicin, epirubicin, mitoxantrone, losoxantrone
- groups I and II topoisomerases such as etoposide, teniposide, amsacrine, irinotecan, topotecan and tomudex
- fluoropyrimidines such as 5-fluorouracil, UFT, floxuridine
- cytidine analogues such as 5-azacytidine, cytarabine, gemcitabine, 6-mercaptopurine, 6-thioguanine
- adenosine analogues such as pentostatin, cytarabine or fludarabine phosphate
- methotrexate and folinic acid
- various enzymes and compounds such as L-asparaginase, hydroxyurea, trans-retinoic acid, suramin, dexrazoxane, amifostine, herceptin as well as oestrogenic and androgenic hormones
- antivascular agents such as combretastatin derivatives, for example CA4P, chalcones or colchicine, for example ZD6126, and their prodrugs
- kinase inhibitors such as ertonilib or imatinib
- biotherapeutic agents such as antibodies such as rituximab, bevacizumab, cetuximab, trastuzumab or alemtuzumab
- proteasome inhibitors such as bortezomib.

It is also possible to combine the compounds of the present invention with a radiation treatment. These treatments may be administered simultaneously, separately or sequentially. The treatment will be adapted by the practitioner according to the disease to be treated.

What is claimed is:
1. An compound compound of formula I:

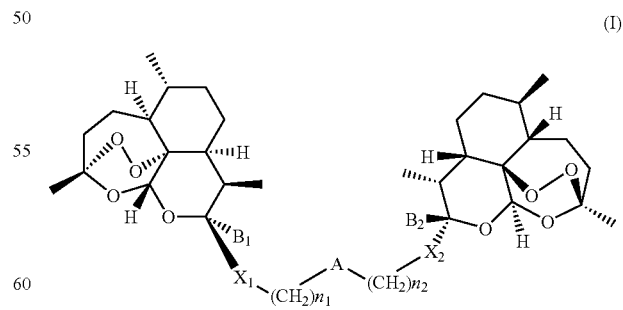

wherein
A is a divalent group selected from the group consisting of S, SO, SO$_2$, N(CH$_3$), N(CH$_2$—C(O)O—CH$_2$CH$_3$), N(CH$_2$—COOH), (C$_1$-C$_6$)alkenylene, NHCO, 1,2,3-triazole, and NHSO$_2$;

$B_1$ and $B_2$ are both $CF_3$;

$X_1$ and $X_2$ are both O;

$n_1$ and $n_2$ are independently selected from the group consisting of 1, 2, 3 or 4; or pharmaceutically acceptable salt thereof, wherein the compound has less than 10 μM IC50 against HCT116 tumor line.

2. The compound of claim 1 or a hydrate, solvate, or pharmaceutically acceptable salt thereof, wherein $n_1$ and $n_2$ are identical and are selected from the group consisting of 2, 3 and 4.

3. The compound of claim 1, or pharmaceutically acceptable salt thereof, wherein A is selected from the group consisting of $N(CH_2C(O)OCH_2CH_3$, and $N(CH_2COOH)$ and $n_1$ and $n_2$ are both 2.

4. The compound of claim 1, or pharmaceutically acceptable salt thereof, wherein A is ($C_1$-$C_6$)alkenylene and $n_1$ and $n_2$ are both 1.

5. The compound of claim 1, or pharmaceutically acceptable salt thereof, wherein A is selected from the group consisting of NHCO, and 1,2,3-triazole, and $n_1$ and $n_2$ are independently selected from the group consisting of 1 and 2.

6. A compound selected from the group consisting of:
(3S,5aS,6R,8aS,9R,10R,12R,12aR,3'S,5'aS,6'R,8'aS,9'R,10'R,12'R,12'aR)-10,10'-[thiobis(2,1-ethanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R,10'R,12'R,12'aR)-10,10'-[sulfinylbis(2,1-ethanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R,10'R,12'R,12'aR)-10,10'-[sulfonylbis(2,1-ethanediyloxy)]bis[decahydro-3,6,9-trimethyl-10-trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R,10'R,12'R,12'aR)-10,10'-[thiobis(3,1-propanediyloxy)]bis[decahydro-3,6,9-trimethyl-10-(trifluoromethyl)-3,12-epoxy-12H-pyrano[4,3-j]-1,2-benzodioxepine;

5aS,6R,8aS,9R,10R,12R,12aR,3'S,5'aS,6'R,8'aS,9'R,10'R,12'R,12'aR)-10,10'-[sulfinylbis(3,1-propanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R,10'R,12'R,12'aR)-10,10'-[sulfonylbis(3,1-propanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R,10'R,12'R,12'aR)-10,10'-[thiobis(4,1-butanediyloxy)]bis[decahydro-3,6,9-trimethyl-10-(trifluoromethyl)-3,12-epoxy-12H-pyrano[4,3-j]-1,2-benzodioxepine;

2-[[(3R,5aS,6R,8aS,9R,10R,12R,12aR)-decahydro-3,6,9-trimethyl-10-(trifluoromethyl)-3,12-epoxy-12H-pyrano[4,3-j]-1,2-benzodioxepin-10-yl]oxy]-N-[2-[[(3R,5aS,6R,8aS,9R,10R,12R,12aR)-decahydro-3,6,9-trimethyl-10-(trifluoromethyl)-3,12-epoxy-12H-pyrano[4,3-j]-1,2-benzodioxepin-10-yl]oxy]ethyl]-N-methylethanamine;

2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}-N-(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)ethanamine;

ethyl N,N-bis(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)glycinate;

N,N-bis(2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)glycine;

2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}-N-(2-{[(3S,5aS,6R,8aS,9R,10R,-12R,12aR)-3,6,9-trimethyl-10-(trifluoromethyl)decahydro-3,12-epoxy[1,2]dioxepino[4,3-i]isochromen-10-yl]oxy}ethyl)acetamide; 5aS,6R,8aS,9R,10R,12R,12aR,3'S,5'aS,6'R,8'aS,9'R,10'R,12'R,12'aR)-10,10'-[(2E)-but-2-ene-1,4-diylbis(oxy)]bis[3,6,9-trimethyl-10-(trifluoromethyl)decahydro-3,12-epoxy[1,2]dioxepino[4,3-i]isochromene];

(3S,5aS,6R,8aS,9R,10R,12R,12aR,3'S,5'aS,6'R,8'aS,9'R,10'R,12'R,12'aR)-10,10'-[(2Z)-but-2-ene-1,4-diylbis(oxy)]bis[3,6,9-trimethyl-10-(trifluoromethyl)decahydro-3,12-epoxy[1,2]dioxepino[4,3-i]isochromene];

(3S,5aS,6R,8aS,9R,10R,12R,12aR,3'S,5'aS,6'R,8'aS,9'R,10'R,12'R,12'aR)-10,10'-[(2R,3R)-oxirane-2,3-diylbis(methyleneoxy)]bis[3,6,9-trimethyl-10-(trifluoromethyl)-decahydro-3,12-epoxy[1,2]dioxepino[4,3-i]isochromene];

(1-(2-{[(3S,5aS,6R,8aS,9R,10R,12R,12aR)-3,6,9-trimethyl-10-(trifluoromethyl)deca-hydro-3,12-epoxy[1,2]dioxepino[4,3-i]isochromen-10-yl]oxy}ethyl)-4-({[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}methyl)-1H-1,2,3-triazole; and 1-(2-{[(3S,5aS,6R,8aS,9R,10R,12R,12aR)-3,6,9-trimethyl-10-(trifluoromethyl)deca-hydro-3,12-epoxy[1,2]dioxepino[4,3-i]isochromen-10-yl]oxy}ethyl)-5-({[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}ethyl)-1H-1,2,3-triazole or pharmaceutically acceptable salt thereof.

7. A pharmaceutical composition comprising a compound of formula I:

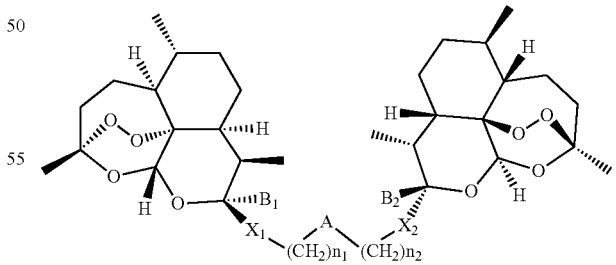

(I)

wherein

A is a divalent group selected from the group consisting of S, SO, $SO_2$, $N(CH_3)$, $N(CH_2—C(O)O—CH_2CH_3)$, $N(CH_2—COOH)$, ($C_1$-$C_6$)alkenylene, NHCO, 1,2,3-triazole, and $NHSO_2$;

$B_1$ and $B_2$ are both $CF_3$;

$X_1$ and $X_2$ are both O;

n₁ and n₂ are independently selected from the group consisting of 1, 2, 3 or 4; or a hydrate, solvate, or pharmaceutically acceptable salt thereof and at least one pharmaceutically acceptable excipient.

8. The pharmaceutical composition of claim 7, wherein $n_1$ and $n_2$ are identical and are selected from the group consisting of 2, 3 and 4.

9. The pharmaceutical composition of claim 7, wherein A is selected from the group consisting of, N(CH₂C(O)OCH₂CH₃), and N(CH₂COOH, and $n_1$ and $n_2$ are both 2.

10. The pharmaceutical composition of claim 7, wherein A is (C₁-C₆)alkenylene and $n_1$ and $n_2$ are both 1.

11. The pharmaceutical composition of claim 7, wherein A is selected from the group consisting of NHCO and 1,2,3-triazole, and $n_1$ and $n_2$ are independently selected from the group consisting of 1 and 2.

12. The pharmaceutical composition of claim 7, wherein the compound is selected from the group consisting of:

5aS,6R,8aS,9R,10R,12R,12aR,3'S,5'aS,6'R,8'aS,9'R, 10'R,12'R,12'aR)-10,10'-[thiobis(2,1-ethanediyloxy)]bis[decahydro-3,6,9-trimethyl-10-(trifluoromethyl)-3, 12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[sulfinylbis(2,1-ethanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[sulfonylbis(2,1-ethanediyloxy)]bis[decahydro-3,6,9-trimethyl-10-trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[thiobis(3,1-propanediyloxy)]bis[decahydro-3,6,9-trimethyl-10-(trifluoromethyl)-3, 12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[sulfinylbis(3,1-propanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[sulfonylbis(3,1-propanediyloxy)]bis[decahydro-3,6,9-trimethyl-10-(trifluoromethyl)-3,12-epoxy-12H-pyrano[4,3-j]-1,2-benzodioxepine;

(3S,5aS,6R,8aS,9R,10R,12R,12aR,3'S,5'aS,6'R,8'aS,9'R, 10'R,12'R,12'aR)-10,10'-[thiobis(4,1-butanediyloxy)]bis[decahydro-3,6,9-trimethyl-10-(trifluoromethyl)-3, 12-epoxy-12H-pyrano[4,3-j]-1,2-benzodioxepine;

2-[[(3R,5aS,6R,8aS,9R,10R,12R,12aR)-decahydro-3,6, 9-trimethyl-10-(trifluoromethyl)-3,12-epoxy-12H-pyrano[4,3-j]-1,2-benzodioxepin-10-yl]oxy]-N-[2-[[(3R,5aS,6R,8aS,9R,10R,12R,12aR)-decahydro-3,6, 9-trimethyl-10-(trifluoromethyl)-3,12-epoxy-12H-pyrano[4,3-j]-1,2-benzodioxepin-10-yl]oxy]ethyl]-N-methylethanamine;

2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}-N-(2-{[(3S,5aS, 6R,8aS,9R,10R,12R,12aR)-3,6,9-trimethyl-10-(trifluoromethyl)decahydro-3,12-epoxy[1,2]dioxepino [4,3-i]isochromen-10-yl]oxy}ethyl)ethanamine;

ethyl N,N-bis(2-{[(3S,5aS,6R,8aS,9R,10R,12R,12aR)-3, 6,9-trimethyl-10-(trifluoromethyl)decahydro-3,12-epoxy[1,2]dioxepino[4,3-i]isochromen-10-yl]oxy}ethyl) glycinate;

N,N-bis(2-{[(3S,5aS,6R,8aS,9R,10R,12R,12aR)-3,6,9-trimethyl-10-(trifluoromethyl)decahydro-3,12-epoxy [1,2]dioxepino[4,3-i]isochromen-10-yl]oxy}ethyl)glycine;

2-{[(3S,5aS,6R,8aS,9R,10R,12R,12aR)-3,6,9-trimethyl-10-(trifluoromethyl)decahydro-3,12-epoxy[1,2]dioxepino[4,3-i]isochromen-10-yl]oxy}-N-(2-{[(3S,5aS, 6R,8aS,9R,10R,-12R,12aR)-3,6,9-trimethyl-10-(trifluoromethyl)decahydro-3,12-epoxy[1,2]dioxepino [4,3-i]isochromen-10-yl]oxy}ethyl)acetamide;

(3S,5aS,6R,8aS,9R,10R,12R,12aR,3'S,5'aS,6'R,8'aS,9'R, 10'R,12'R,12'aR)-10,10'-[(2E)-but-2-ene-1,4-diylbis (oxy)]bis[3,6,9-trimethyl-10-(trifluoromethyl)decahydro-3,12-epoxy[1,2]dioxepino[4,3-i]isochromene];

(3S,5aS,6R,8aS,9R,10R,12R,12aR,3'S,5'aS,6'R,8'aS,9'R, 10'R,12'R,12'aR)-10,10'-[(2Z)-but-2-ene-1,4-diylbis (oxy)]bis[3,6,9-trimethyl-10-(trifluoromethyl)decahydro-3,12-epoxy[1,2]dioxepino[4,3-i]isochromene];

(3S,5aS,6R,8aS,9R,10R,12R,12aR,3'S,5'aS,6'R,8'aS,9'R, 10'R,12'R,12'aR)-10,10'-[(2R,3R)-oxirane-2,3-diylbis (methyleneoxy)]bis[3,6,9-trimethyl-10-(trifluoromethyl)-decahydro-3,12-epoxy[1,2]dioxepino[4,3-i] isochromene];

(1-(2-{[(3S,5aS,6R,8aS,9R,10R,12R,12aR)-3,6,9-trimethyl-10-(trifluoromethyl)deca-hydro-3,12-epoxy[1,2] dioxepino[4,3-i]isochromen-10-yl]oxy}ethyl)-4-({[(3S,5aS,6R,8aS,9R,10R,12R,12aR)-3,6,9-trimethyl-10-(trifluoromethyl)decahydro-3,12-epoxy[1,2] dioxepino[4,3-i]isochromen-10-yl]oxy}methyl)-1H-1, 2,3-triazole; and 1-(2-{[(3S,5aS,6R,8aS,9R,10R,12R,12aR)-3,6,9-trimethyl-10-(trifluoromethyl)deca-hydro-3,12-epoxy[1,2] dioxepino[4,3-i]isochromen-10-yl]oxy}ethyl)-5-({[(3S,5aS,6R,8aS,9R,10R,12R,12aR)-3,6,9-trimethyl-10-(trifluoromethyl)decahydro-3,12-epoxy[1,2] dioxepino[4,3-i]isochromen-10-yl]oxy}ethyl)-1H-1,2, 3-triazole or pharmaceutically acceptable salt thereof.

13. A method for treating cancer in a patient in need thereof, comprising administering to such patient an effective amount of a compound of claim 1 or pharmaceutically acceptable salt thereof.

\* \* \* \* \*